US012778757B2

(12) United States Patent
Hassler et al.

(10) Patent No.: US 12,778,757 B2
(45) Date of Patent: Nov. 3, 2026

(54) IMPLANT FOR REPAIR AND REGENERATION OF SOFT TISSUE

(71) Applicant: TORNIER, Montbonnot Saint Martin (FR)

(72) Inventors: Michel Hassler, Saint Ismier (FR); Ghassene Ouenzerfi, Saint Martin d'Hères (FR)

(73) Assignee: TORNIER (FR)

(*) Notice: Subject to any disclaimer, the term of this patent is extended or adjusted under 35 U.S.C. 154(b) by 1081 days.

(21) Appl. No.: 17/819,718

(22) Filed: Aug. 15, 2022

(65) Prior Publication Data

US 2022/0387179 A1 Dec. 8, 2022

Related U.S. Application Data

(63) Continuation of application No. 16/772,595, filed as application No. PCT/EP2018/085329 on Dec. 17, 2018, now abandoned.

(30) Foreign Application Priority Data

Dec. 18, 2017 (EP) .................................... 17306797

(51) Int. Cl.
*A61F 2/30* (2006.01)
*A61F 2/64* (2006.01)
(Continued)

(52) U.S. Cl.
CPC ............ *A61F 2/30756* (2013.01); *A61F 2/64* (2013.01); *A61F 2002/30242* (2013.01);
(Continued)

(58) Field of Classification Search
CPC ................... A61F 2/30756; A61F 2/64; A61F 2002/30242; A61F 2002/4228;
(Continued)

(56) References Cited

U.S. PATENT DOCUMENTS

| | | | |
|---|---|---|---|
| 4,846,840 | A | 7/1989 | Leclercq |
| 5,743,918 | A | 4/1998 | Calandruccio et al. |

(Continued)

FOREIGN PATENT DOCUMENTS

| | | | |
|---|---|---|---|
| EP | 2468217 | A1 | 6/2012 |
| WO | 2007041375 | A2 | 4/2007 |

(Continued)

OTHER PUBLICATIONS

International Search Report and Written Opinion for International Application No. PCT/EP2018/085329 filed Dec. 17, 2018, 12 pages.

(Continued)

*Primary Examiner* — Sarah W Aleman
*Assistant Examiner* — Melissa A Hoban
(74) *Attorney, Agent, or Firm* — DUANE MORRIS LLP

(57) ABSTRACT

Provided is a method of stimulating regeneration of cartilage in an area of diseased cartilage in a layer of cartilage in a first bone of a joint. The method includes forming a first recess in the first bone at the area of diseased cartilage, and positioning a first spherical implant within the first recess, where the first spherical implant is dimensioned to be smaller than the first recess so that the first spherical implant is capable of moving in two dimensions within the first recess resulting in shear forces between the first spherical implant and the cartilage and stimulates formation of fibrous tissue which subsequently transforms into cartilage.

20 Claims, 27 Drawing Sheets

(51) Int. Cl.
*A61F 2/42* (2006.01)
*A61F 2/66* (2006.01)

(52) U.S. Cl.
CPC ................. *A61F 2002/4228* (2013.01); *A61F 2002/4243* (2013.01); *A61F 2002/4274* (2013.01); *A61F 2002/6635* (2013.01); *A61F 2310/00161* (2013.01)

(58) Field of Classification Search
CPC ...... A61F 2002/4243; A61F 2002/4274; A61F 2002/6635; A61F 2310/00161; A61F 2002/30672; A61F 2002/30762; A61F 2310/00005
See application file for complete search history.

(56) References Cited

U.S. PATENT DOCUMENTS

| | | | |
|---|---|---|---|
| 2001/0039455 A1 | 11/2001 | Simon et al. | |
| 2004/0133276 A1 | 7/2004 | Lang et al. | |
| 2006/0129071 A1 | 6/2006 | Hauselmann et al. | |
| 2008/0215156 A1 | 9/2008 | Duggal et al. | |
| 2009/0228106 A1* | 9/2009 | Strzepa | A61F 2/30756 623/14.12 |
| 2010/0161073 A1 | 6/2010 | Thomas et al. | |
| 2013/0304226 A1 | 11/2013 | Ritz et al. | |

FOREIGN PATENT DOCUMENTS

| | | |
|---|---|---|
| WO | 2008120215 A2 | 10/2008 |
| WO | 2013150537 A1 | 10/2013 |
| WO | 2019151578 A1 | 6/2019 |

OTHER PUBLICATIONS

Communication Pursuant to Article 94(3) issued in connection with European Patent Application No. 18819112.6, Jan. 30, 2024, 7 pages.
Extended European Search Report issued in connection with European Patent Application No. 25201403.0, Nov. 20, 2025.
Guademaris, et al., "Positive Impact of Pyrocarbon and Mechanical Loading on Cartilage-Like Tissue Synthesis in a Scaffold-Free Process—Science Direct", Journal of Bioscience and Bioengineering, vol. 139, No. 1, Jan. 1, 2025, 14 pages.

* cited by examiner

Lateral view of the talus

B
A
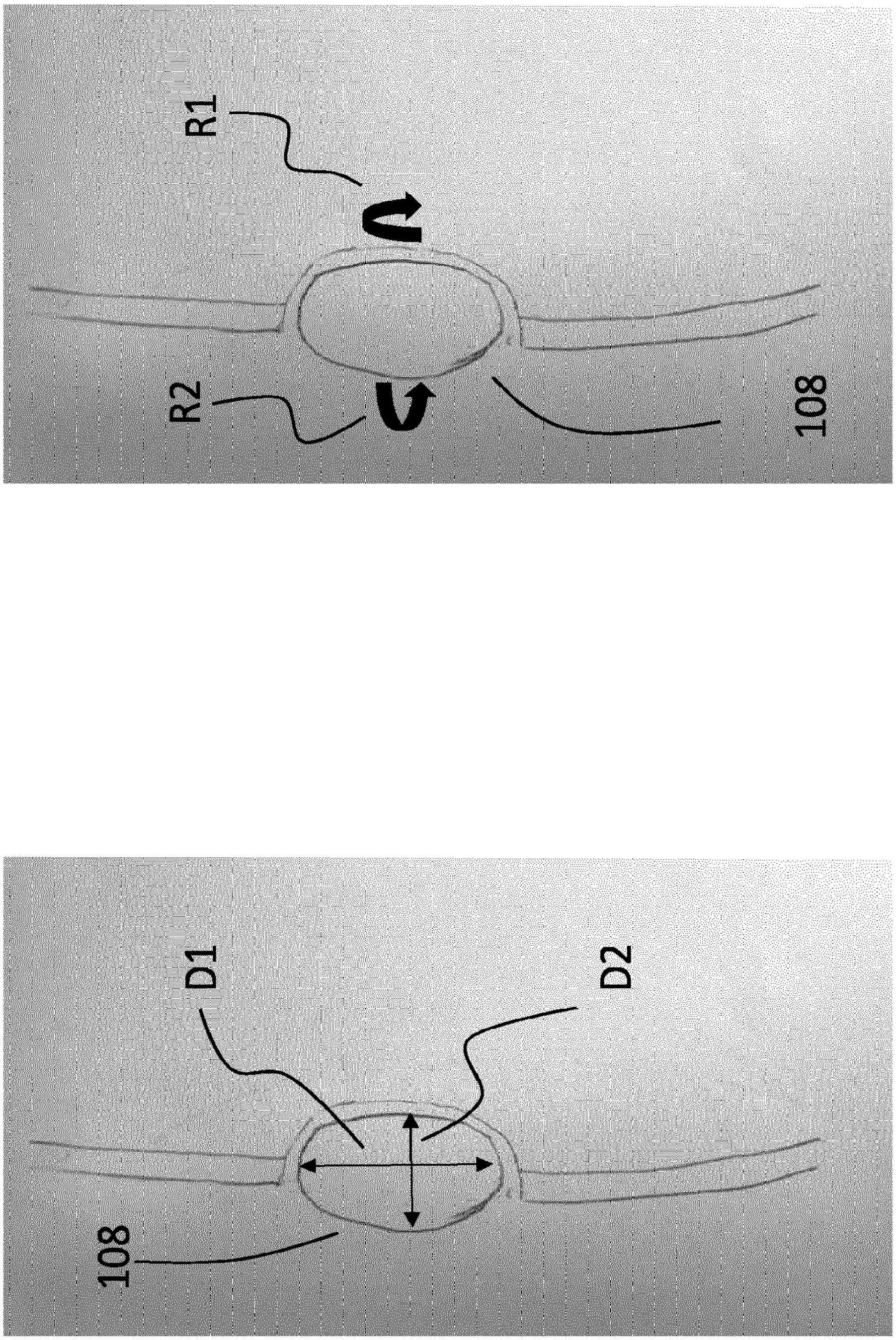
*FIG. 22A-B*

A

B

FIG. 23C-D
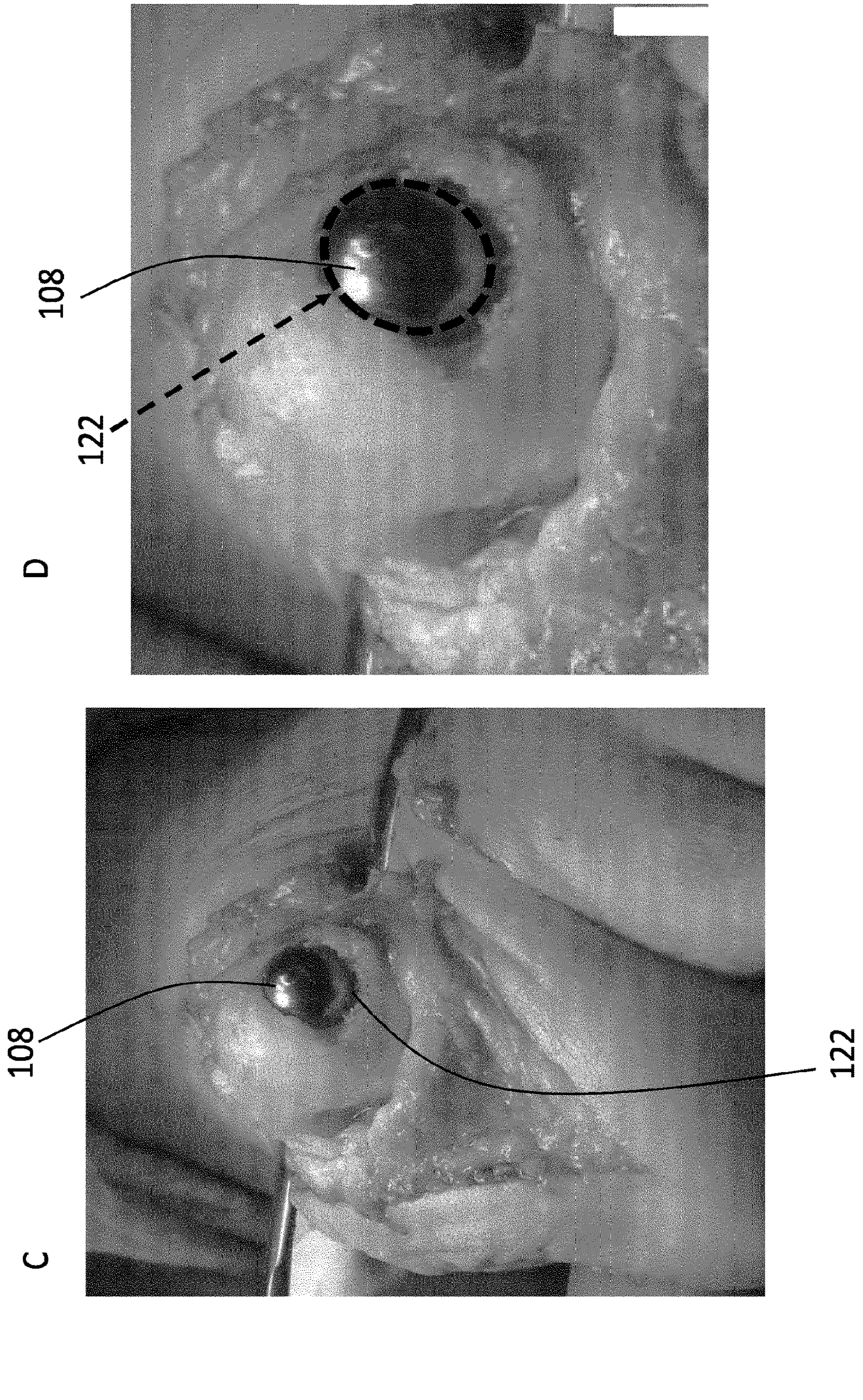

108

E

IMPLANT FOR REPAIR AND REGENERATION OF SOFT TISSUE

RELATED APPLICATIONS

This application is a continuation of co-pending U.S. patent application Ser. No. 16/772,595, filed on Jun. 12, 2020, which is the U.S. National Phase under 35 U.S.C. § 371 of International Patent Application No. PCT/EP2018/085329, filed Dec. 17, 2018, which claims priority to European Patent Application No. 17306797.6, filed Dec. 18, 2017, the entire contents of each of which is incorporated by reference herein.

FIELD

The present disclosure relates generally to implants and their use in the repair or regeneration of soft tissues, such as the cartilage located between joints.

DESCRIPTION OF THE RELATED ART

Cartilage acts as a pad between bones to reduce friction and prevent the bones from grinding against one another. Cartilage covers the articular surface of many, if not all, joints in the body. The smoothness and thickness of the cartilage are factors that determine the load-bearing characteristics and mobility of the joints. Over time, due to injury or heredity, however, lesions such as fissures, cracks or crazes can form in the cartilage. In some cases, osteochondral, the lesion penetrates to the subchondral surface of the bone. In other cases, chondral, the lesion does not penetrate to the subchondral surface of the bone. In any event, lesions generally do not repair themselves—and if any repair is made it is insufficient to heal—leading to significant pain and disability, either acutely or over time.

One approach for regenerating new cartilage is autologous chondrocyte transplantation. However, this technique is complex and relatively costly. Other techniques, aimed at repair instead of regeneration, include debridement, lavage, microfracturing, drilling, and abrasion arthroplasty. These procedures generally involve penetrating the region of vascularization in the subchondral bone with an instrument until bleeding occurs. Formation of a fibrin clot differentiates into fibrocartilage, which then covers the defect site. Some have found, however, that the resulting repair tissue is relatively weak, disorganized, and lacks the biomechanical properties of normal hyaline cartilage that typically covers the bone ends. Additionally, this technique can generally only be used on chondral defects in the presence of normal joint congruity.

An alternative approach has been to undergo a total replacement of the joint. Such total replacements, however, are costly, high risk, and involve a long recovery time. Accordingly, there is a need for alternative treatments.

SUMMARY

The present disclosure provides for implants for repair and/or regeneration of soft tissue, such as cartilage. Methods of using implants are also provided for. For example, in several embodiments, there is provided for the use of an implant for regeneration of cartilage, the implant comprising at least two regions, the first region comprising an anchoring region, the anchoring region configured to be positioned at least partially within a layer of bony tissue that underlies a layer of cartilage, the second region comprising a stimulating region, the stimulating region configured to be positioned at least partially within the treatment region. As used herein, the term "anchoring region" shall be given its ordinary meaning and shall also refer to a portion of an implant, according to several embodiments, that is positioned more distally with respect to a joint space (e.g., a first portion of the implant is located closer to a joint space (or in the joint space) as compared to a second portion of the implant that is located more distally). In several embodiments, the anchoring region allows for retention of the implant in one or two axes, yet allows for micro-movements of the implant. While an anchoring/retention region does serve to at least partially retain the implant in a recess that is formed, the region also allows for movement in limited degrees of freedom (e.g., lateral, linear or rotational movements). In several embodiments, the layer of cartilage is positioned along a surface of the bony tissue. In several embodiments, the layer of cartilage comprises an area of cartilage that is damaged or diseased, said area defining a treatment region, and an area of healthy cartilage. In several embodiments, the layer of cartilage has a depth defined by a distance between a surface of the healthy cartilage distal to the surface of the bony tissue and a surface of the healthy cartilage contacting/juxtaposed with the surface of the bony tissue. In several embodiments, the stimulating region comprises an arcuate surface and the arcuate surface is dimensioned to create a discontinuous surface between the arcuate surface of the implant and the healthy cartilage at a position where the arcuate surface is positioned at a margin between the treatment region and the healthy cartilage. In several embodiments, the stimulating region interacts with the layer of cartilage and results in regeneration of cartilage.

In several embodiments, the arcuate surface of the stimulating region comprises a convex upper face having a perimeter edge, wherein the perimeter edge is the portion of the arcuate surface of the stimulating region positioned at the margin. In one embodiment, the convex upper face has a diameter of between about 5 and about 100 mm. In several embodiments, the diameter of the implant is configured to approximate a defect in cartilaginous tissue of a subject, such that the stimulation of cartilage reformation results in the repair of the defect. For example, in several embodiments, the convex upper face has a diameter of between about 10 and about 60 mm. In several embodiments, the implant is configured for use in the shoulder, or other "ball and socket" joint. In several embodiments, the convex upper face has a diameter of between about 10 and about 25 mm. In several such embodiments, the implant is configured for use in an interphalangeal joint. For example, in one embodiment the implant is configured for use in a metacarpophalangeal joint. In additional embodiments, the implant is configured for use in a metatarsophalangeal joint.

In several embodiments, the discontinuous surface is generated by the arcuate surface having a height that is less than then depth of the layer of cartilage at the margin, thereby resulting in a step-down from the distal surface of the healthy cartilage to the arcuate surface. Alternatively, in several embodiments, the discontinuous surface is generated by the arcuate surface having a radius of curvature that is less than a radius of curvature defined by the healthy cartilage surrounding the treatment zone, thereby resulting in a step-down from the distal surface of the healthy cartilage to the arcuate surface.

Depending on the embodiment, the discontinuous surface can comprise a step-down having a height ranging between about 0.05 and about 5 mm, as measured from the perimeter of the arcuate surface to the surface of the healthy cartilage distal to the surface of the bony tissue. In several embodiments, the arcuate surface comprises the convex upper face juxtaposed with a concave lower face, the concave lower face configured to be positioned within the treatment region.

In several embodiments, the anchoring region comprises a stem configured to interact with a receiving element, the receiving element being threaded into the bony tissue. In one embodiment, the stem comprises a Morse taper. In several embodiments, the implant is a cap and stem with the stem being positioned directly into the bony tissue (e.g., without use of an independent anchoring structure).

In several embodiments, all or a portion of the implant comprises pyrocarbon. In additional embodiments, all or a portion of the stimulating region comprises pyrocarbon.

In several embodiments, the discontinuous surface results in shear forces between the stimulating region of the implant and the healthy cartilage. In several embodiments, the shear forces between the stimulating region of the implant and the healthy cartilage stimulate formation of fibrous tissue. In several such embodiments, the formed fibrous tissue is transformed to articular cartilage.

In several embodiments, the anchoring region and stimulating region are mirror images of one another. In some such embodiments, the implant is configured to be 4 positioned in a recessed area, wherein the recessed area passes through the treatment region and extends into the bony tissue.

In one embodiment, the recessed area extends through a layer of cortical bone and at least partially extends into cancellous bone. In several embodiments, the implant is a sphere.

In several embodiments, the discontinuous region comprises a step-up. In several embodiments, the step-up has a height of about 0.05 to about 3 mm, as measured from the layer of cartilage (e.g., between the upper surface of the cartilage and the upper surface of the implant at the margin where the perimeter of the implant meets the cartilage). In some embodiments, a diameter of the recessed area in the layer of cartilage is less than a diameter of the recessed area in the bony tissue, and wherein the reduced diameter aids in retaining the implant within the recessed area.

In several embodiments, the discontinuous region comprises a step-down. In several such embodiments, the step-down has a height of about 0.05 to about 5 mm, as measured from the layer of cartilage (e.g., between the upper surface of the cartilage and the upper surface of the implant at the margin where the perimeter of the implant meets the cartilage). In several embodiments, a diameter of the recessed area in the layer of cartilage is approximately equivalent to a diameter of the recessed area in the bony tissue, and wherein the implant is within the recessed area through the interaction of the anchoring region with the recessed area and by pressure from an opposing tissue on the implant.

In several embodiments, the implant is configured to be movable within the recessed area. In several such embodiments, the motion of the implant comprises motion in two dimensions. In several embodiments, the two dimensional motion results in shear forces between the stimulating region of the implant and the healthy cartilage. In several embodiments, the shear forces between the stimulating region of the implant and the healthy cartilage stimulate formation of fibrous tissue. In one embodiment, the formed fibrous tissue is transformed to articular cartilage.

In several embodiments, there is provided a plurality of spherical pyrocarbon implants for repair of cartilage by implantation in a single joint space, the implants being configured to be implanted in a plurality of corresponding recesses in bony tissue, the bony tissue being overlayed by a layer of cartilage, wherein the recesses in the bony tissue extends through the layer of cartilage, through a layer of cortical bone, and at least partially extends into a layer of cancellous bone, wherein the layer of cartilage comprises a least one region of damaged cartilage (depicted in the Figures as 500), the implants being dimensioned to be smaller than each corresponding recessed area such that each of the plurality implants is capable of moving in two dimensions within the recessed area, wherein the motion of the implant within the recessed area results in shear forces between the implant and the cartilage, wherein the shear forces between the implant and the cartilage stimulates formation of fibrous tissue, and wherein the formed fibrous tissue is transformed to articular cartilage, thereby repairing the cartilage.

Also provided for, in several embodiments, is an implant for repair of cartilage by implantation in a joint space, the implant being pyrocarbon and spherical in shape, the implant being configured to be implanted in a corresponding recessed area formed in bony tissue, the bony tissue being overlayed by a layer of cartilage, wherein the layer of cartilage comprises a least one region of damaged cartilage, the implant being dimensioned to be smaller than the corresponding recessed area, such that implant is capable of moving in two dimensions within the recessed area.

In several embodiments, the recessed area in the bony tissue extends through the layer of cartilage, through a layer of cortical bone, and at least partially extends into a layer of cancellous bone. In several embodiments, the motion of the implant within the recessed area results in shear forces between the implant and the cartilage, such shear forces between the implant and the cartilage stimulating formation of fibrous tissue, and the formed fibrous tissue being subsequently transformed to articular cartilage, thereby repairing the cartilage.

Also provided for herein is the use of an implant for the repair of a region of damaged or defective soft tissue, the region of damaged or defective soft tissue being located within a region of normal soft tissue and comprising a sub-region of reduced or lost soft tissue as compared to the region of normal soft tissue, the normal soft tissue overlaying or being positioned between two bony surfaces, the soft tissue comprising cartilage, the sub-region of reduced or lost soft tissue having a length, a width and a depth, the implant having dimensions enabling the implant to be at least partially positioned within the sub-region of soft tissue, the dimensions comprising a width as measured from a central axis of the implant and a height as measured from a plane of the implant that is perpendicular to said central axis. In several embodiments, the height of the implant is greater in a region about the central axis as compared to a lateral region located about the width of the implant, and in some such embodiments, upon placement of the implant at least partially within the sub-region of soft tissue, the lateral region is positioned in the sub-region of reduced or lost soft tissue such that the depth of the sub-region is greater than the height of the implant at the lateral region.

Also provided for is the use of an implant for stimulating regeneration of cartilage, the implant comprising at least two portions, the first portion comprising an anchoring 6 portion, the anchoring portion configured to be positioned below a plane associated with a region of healthy cartilage, the plane having a depth defined by an apical and basal surface of the region of healthy cartilage, the second portion comprising a stimulating portion, the stimulating portion configured to be positioned at least partially within the plane associated with the region of healthy cartilage, wherein the second portion comprises a dome shape having a height that is greatest at a position along a central axis of the implant, the height decreasing towards a lateral region of the dome shaped second portion, wherein the height of the lateral region of the dome shaped second portion is different than the depth of the plane of the region of healthy cartilage.

In several embodiments, multiple implants can be used in a single joint space to repair a defect in cartilage or other soft tissue. For example, there is provided for herein a plurality of spherical pyrocarbon implants for repair of cartilage by implantation in a single joint space, the plurality implants being configured to be implanted in a recessed area in bony tissue, the bony tissue being overlayed by a layer of cartilage, the plurality of implants being dimensioned to be placed in the recessed area such that each of the plurality implants is capable of moving in multiple dimensions within the recessed area. In several embodiments, the recessed area in the bony tissue extends through the layer of cartilage, through a layer of cortical bone, and at least partially extends into a layer of cancellous bone, and in several embodiments the layer of cartilage comprises a least one region of damaged cartilage. In several embodiments, the motion of the implants within the recessed area results in shear forces between the implants and the cartilage, wherein the shear forces between the implants and the cartilage stimulates formation of fibrous tissue, and wherein the formed fibrous tissue is transformed to articular cartilage, thereby repairing the cartilage.

There are also provided for herein various methods for the repair of cartilage. For example, in several embodiments there is provide a method for the repair of cartilage, comprising, identifying a layer of cartilage positioned along a surface of a bony tissue, forming a first recess in the bony tissue, wherein the recess passes through the layer of cortical bone and at least partially into the layer of cancellous bone, inserting an implant into the first recess, the implant comprising an anchoring region and a stimulating region comprising an arcuate surface.

In several embodiments, the layer of cartilage comprises an area of cartilage that is damaged or diseased, said area defining a treatment region, and an area of healthy cartilage, wherein the bony tissue underlies the layer of cartilage and comprises a layer of cortical bone and a layer of cancellous bone, wherein the layer of cartilage has a depth defined by a distance between a surface of the healthy cartilage distal to the surface of the bony tissue and a surface of the healthy cartilage contacting the surface of the bony tissue. In several embodiments, the anchoring region is configured to be positioned at least partially within the layer of cancellous bone, wherein the stimulating region is configured to be positioned at least partially within the treatment region, wherein the arcuate surface of the stimulating region is dimensioned to create a discontinuous surface between the arcuate surface of the implant and the healthy cartilage at a position where the arcuate surface is positioned at a margin between the treatment region and the healthy cartilage, and wherein the stimulating region interacts with the layer of cartilage and results in regeneration of cartilage, thereby repairing the cartilage.

Also provided for herein are methods of repairing cartilage wherein the arcuate surface of the stimulating region comprises a convex upper face having a perimeter edge, wherein the perimeter edge is the portion of the arcuate surface of the stimulating region positioned at the margin. In several embodiments, the convex upper face has a diameter of between about 5 and about 100 mm. In one embodiment, the convex upper face has a diameter of between about 10 and about 60 mm. In one embodiment, the layer of cartilage is located in the shoulder and the first recess is formed in the humerus. In several embodiments, the method further comprises forming at least one additional recess, wherein the additional recess is formed in the humerus or in the scapula. In one embodiment, the convex upper face has a diameter of between about 10 and about 25 mm. In some such embodiments, the implant is configured for use in an interphalangeal joint, while in other embodiments, the implant is configured for use in a metacarpophalangeal joint and in still additional embodiments the implant is configured for use in a metatarsophalangeal joint. In other embodiments, the implant is configured for use in a knee joint, an acetabulofemoral (hip) joint, a talocrural (ankle) joint, a radiocarpal (wrist) joint, an elbow joint, or any other appropriate joint.

In some embodiments, the discontinuous surface is generated by the arcuate surface having a height that is less than then depth of the layer of cartilage at the margin, thereby resulting in a step-down from the distal surface of the healthy cartilage to the arcuate surface. In other embodiments, the discontinuous surface is generated by the arcuate surface having a radius of curvature that is less than a radius of curvature defined by the healthy cartilage surrounding the treatment zone, thereby resulting in a step-down from the distal surface of the healthy cartilage to the arcuate surface. In several embodiments, the discontinuous surface comprises a step-down having a height ranging between about 0.05 and about 3 mm, as measured from the perimeter of the arcuate surface to the surface of the healthy cartilage distal to the surface of the bony tissue.

In several embodiments, the arcuate surface comprises the convex upper face juxtaposed with a concave lower face, the concave lower face configured to be positioned within the treatment region, the convex upper face having a radius of curvature such that a discontinuity is formed between the convex upper face of the implant and the cartilage at the margin. In several embodiments, the anchoring region comprises a stem configured to interact with a receiving element, the receiving element being threaded into the bony tissue. In one embodiment the stem comprises a Morse taper. In one embodiment, the receiving element is positioned in the recess and at least partially within the cancellous bone layer. In several embodiments, the implant is configured to have the stem function as the anchor (e.g., the stem is directly placed into the cancellous and/or cortical bone). In several embodiments, all or a portion of the implant comprises pyrocarbon. In additional embodiments, all or a portion of the stimulating region comprises pyrocarbon.

In several embodiments, the discontinuous surface results in shear forces between the stimulating region of the implant and the healthy cartilage. In several embodiments, the shear forces between the stimulating region of the implant and the healthy cartilage stimulate formation of fibrous tissue. In several embodiments, the formed fibrous tissue is transformed to articular cartilage.

Further disclosed are methods employing a spherical implant, the method comprising an anchoring region and stimulating region are mirror images of one another, wherein the implant is configured to be positioned in a recessed area, wherein the recessed area passes through the treatment region and extends into the bony tissue.

In several embodiments, the implant is a sphere. In one embodiment, the discontinuous region comprises a step-up. In several embodiments, the step-up has a height of about 0.05 to about 5 mm, as measured from the layer of cartilage. In several embodiments, the diameter of the recessed area in the layer of cartilage is less than a diameter of the recessed area in the bony tissue, and wherein the reduced diameter aids in retaining the implant within the recessed area.

In several embodiments, the discontinuous region comprises a step-down. In several such embodiments, the step-down has a height of about 0.05 to about 5 mm, as measured from the layer of cartilage. In several embodiments, the diameter of the recessed area in the layer of cartilage is approximately equivalent to a diameter of the recessed area in the bony tissue, and wherein the implant is within the recessed area through the interaction of the anchoring region with the recessed area and by pressure from an opposing tissue on the implant.

In several embodiments, the implant is configured to be movable within the recessed area. In several embodiments, the motion of the implant comprises motion in two dimensions. In some such embodiments, the two dimensional motion results in shear forces between the stimulating region of the implant and the healthy cartilage. In some embodiments, the shear force combined with the load of the bone and the implant as well as the articular fluids (e.g., synovial liquid and/or blood) stimulates the formation of cartilage. In some embodiments, a layer of cartilage may be formed in the joint or in any region where the implant and bone are in contact. In several embodiments, the shear forces between the stimulating region of the implant and the healthy cartilage stimulate formation of fibrous tissue. In several embodiments, the formed fibrous tissue is transformed to articular cartilage (e.g., in the joint space and surrounding the stimulating region of the implant). In several embodiments, the there is also formation of cartilage between the implant and the bone (e.g., sandwiched between the implant and the bony tissue. In several embodiments, cortical bone is also formed under the implant (e.g., a layer of new cartilage and a layer of new bone is formed between the implant and the original bone).

In one embodiment, the implant comprises pyrocarbon. In one embodiment, the implant is configured for use in an interphalangeal joint, a metacarpophalangeal joint, a metatarsophalangeal joint, a knee joint, an acetabulofemoral (hip) joint, a talocrural (ankle) joint, a radiocarpal (wrist) joint, an elbow joint, or another type of joint.

Provided for herein are also methods of repairing cartilage, the methods comprising identifying a layer of cartilage within a single joint space, the layer of cartilage positioned along a surface of a bony tissue, wherein the layer of cartilage comprises an area of cartilage that is damaged or diseased, said area defining a treatment region, and an area of healthy cartilage, wherein the bony tissue underlies the layer of cartilage and comprises a layer of cortical bone and a layer of cancellous bone, wherein the layer of cartilage has a depth defined by a distance between a surface of the healthy cartilage distal to the surface of the bony tissue and a surface of the healthy cartilage juxtaposed with the surface of the bony tissue; forming a plurality of recesses in the bony tissue, wherein the each of the recesses passes through the layer of cortical bone and at least partially into the layer of cancellous bone; inserting at least one spherical pyrocarbon implant into a corresponding recess, each implant being dimensioned to be smaller than its corresponding recessed area such that each implant is capable of moving in two dimensions within its corresponding recessed area, wherein the motion of the implant within the recessed area results in shear forces between the stimulating region of the implant and the healthy cartilage and/or the load between the implant and the bone (cancellous or cortical) combined with the surrounding fluid (e.g., synovial fluid and blood), wherein the shear forces between the implant and the surrounding tissue combined with the synovial fluids and load of the bone and the implant stimulate formation of fibrous tissue; and wherein the formed fibrous tissue is transformed to articular cartilage, thereby repairing the cartilage. In several embodiments, the formed fibrous tissue is transformed to articular cartilage (e.g., in the joint space and surrounding the stimulating region of the implant). In several embodiments, the there is also formation of cartilage between the implant and the bone (e.g., sandwiched between the implant and the bony tissue). In several embodiments, cortical bone is also formed under the implant (e.g., a layer of new cartilage and a layer of new bone is formed between the implant and the original bone).

BRIEF DESCRIPTION OF THE DRAWINGS

FIG. 3A depicts an implant according to several embodiments wherein the implant is configured to interact with an anchor implanted in bony tissue. FIG. 3B depicts an implant according to several embodiments wherein the implant comprises a cap and stem, wherein the stem serves as an anchor. FIG. 3B depicts an implant according to several embodiments wherein the implant comprises a cap and extended stem, wherein the stem serves as an anchor.

FIG. 16B also depicts how the new cartilage aids in retaining the implant, even in an articulating joint where the articulation could position the opposing bone in a position where it is not loading the implant.

FIGS. 20A-20B illustrate two different views of a non-limiting embodiment of implants according to several embodiments disclosed herein wherein a plurality of implants are positioned in a concave portion of a joint, such as the glenoid cavity of the shoulder. FIG. 20A illustrates a side view of a concave joint surface (such as the glenoid cavity of the shoulder) with a plurality of implants shown position along the concave surface of the glenoid. Also illustrated are regions where an initial load would be positioned (e.g., in the absence of any implants, such as with the native joint impact) as well as positions where the initial load is placed post implantation of the plurality of implants. FIG. 20B show the facing view of the glenoid cavity with a plurality of implants placed within the concave glenoid surface. The humeral head is shown in phantom merely for reference. FIG. 20C shows an additional non-limiting embodiment wherein a plurality of implants is placed in a convex joint surface, such as the humeral head. FIG. 20D shows an additional non-limiting embodiment wherein both opposing joint surfaces have received at least one implant. Range of motion vis-a-vis the implants is also illustrated schematically. FIG. 20E shows an additional non-limiting embodiment wherein both opposing joint surfaces have received a single implant. Range of motion vis-a-vis the implant is also illustrated schematically. FIG. 20F shows an additional non-limiting embodiments wherein both opposing joint surfaces have received a plurality of implants. Implants positioned within the first joint surface are shown with hash lines, while implants in the opposing joint surface are shown as checkerboard. The humerus as shown in phantom merely for reference. Range of motion vis-a-vis the implants is also illustrated schematically FIG. 21A depicts a non-limiting embodiment wherein a pyrocarbon humeral head is used to replace the native humeral head and at least one implant is shown positioned in the concave portion of the glenoid. FIG. 21B show the facing view of a similar embodiment, wherein a plurality of implants are positioned within the glenoid cavity opposing a pyrocarbon humeral head.

FIGS. 22A-22B show a non-limiting embodiment of an ellipsoid implant according to several embodiments disclosed herein. FIG. 21A depicts certain dimensions of an ellipsoid implant. FIG. 22B depicts certain rotational characteristics of an ellipsoid implant.

FIGS. 23A-23E depict patient data obtained using an implant according to several embodiments disclosed herein. FIG. 23A shows a damaged cartilage surface in the first metatarsophalangeal (MTP) joint of the patient. FIG. 23B depicts a recess formed in the convex surface of the MTP joint where the damaged cartilage was previously located. FIG. 23C depicts positioning of a spherical implant according to several embodiments herein within the recess formed in the MTP joint. FIG. 23D shows an enlargement of the implant in position in the recess of 23C. FIG. 23E shows a postoperative x-ray depicting the location of the implant.

DETAILED DESCRIPTION

General

Figure 1:
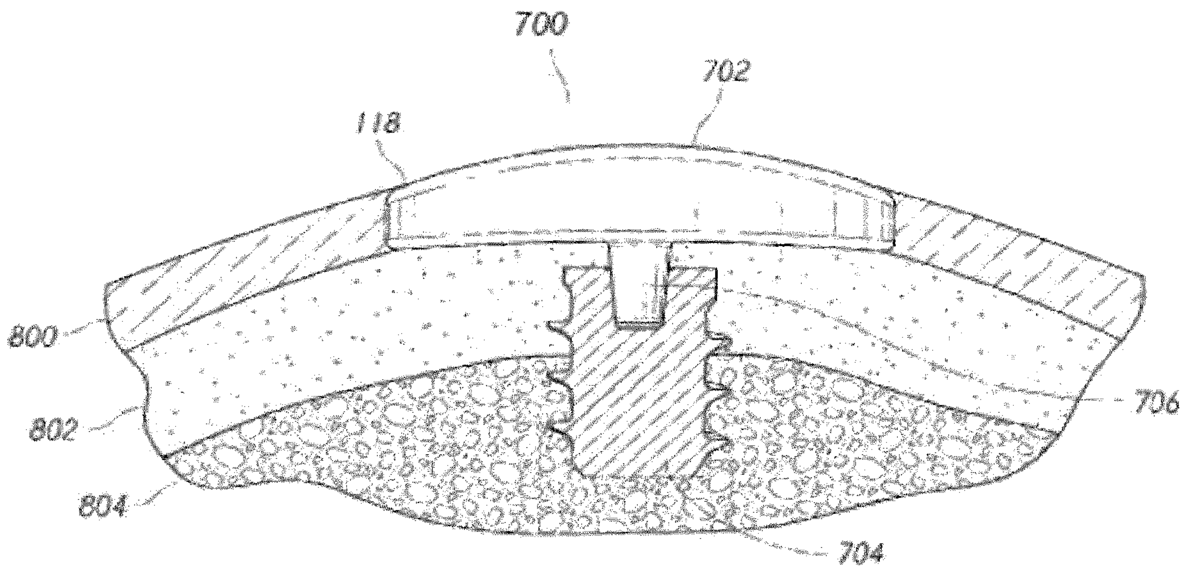
FIG. 1 (Prior Art)
FIG. 1 illustrates a side view of a prior art cap and stem implant.

Cartilage is an elastic-like a tissue that covers and protects the ends of bones where they interact with one another at a joint. Cartilage is produced by specialized cells, known as chondrocytes, that produce a collagen-based extracellular matrix that comprises ground substance that has a high degree of proteoglycans and elastin fibers. Cartilage can be classified into three general types: elastic cartilage, hyaline cartilage, and fibrocartilage. The different types are classified based on their relative amounts of college and proteoglycan. Elastic cartilage, found in the external ear flaps and larynx has the greatest degree of chondrocytes density, and is therefore least flexible. Hyaline cartilage contains fewer cells and is one of the primary types of cartilage found on joint surfaces (e.g. articular cartilage). Fibrocartilage has the least chondrocyte density and is bound, for example in the spinal discs and menisci of certain joints.

Cartilage is avascular and aneural, meaning it has no direct blood supply or connection to the nervous system. Therefore, the chondrocytes obtain the requisite nutrition needed through diffusion. For example, in a joint space, the compression of articular cartilage can generate fluid flow which can assist the delivery of nutrients to the chondrocytes. Moreover, the lack of the vascular supply means that cartilage has a limited capacity for self-repair.

Various options are available for mechanisms to repair or regenerate damaged soft tissue, such as cartilage. For example, bioengineering techniques have been developed to prepare a scaffolding or matrix into which chondrocytes can be placed in vitro to develop artificial cartilage. Additionally, implant devices can be constructed, configured to mimic the shape of a damaged area of cartilage and implanted, thus serving as a replacement for damaged cartilage. However, many implants (unlike certain embodiments of those disclosed herein) are designed and dimensioned to precisely align the implant surface with the contours of the patient's pre-existing articular surface. Such implants are configured in that manner because it was believed that a smooth transition between the implants and the remaining articular cartilage was necessary to properly fill the defect and restore a smooth and continuous joint surface. As shall be described in greater detail below, several embodiments of the implants disclosed herein are purposefully designed to generate a discontinuity (whether in a "positive" (e.g., step-up) or "negative" (e.g., step-down) direction) between a surface of the implants and the native cartilage into which the implant is positioned.

As mentioned above, cartilage protects the ends of long bones and other sites of potential "bone to bone" interaction. Bone, or bony tissue more generally, is made up of several layers. The outer layer of a bone is dense, serves as a protective layer (for the inner layers of the bone and marrow cavity), and is known as cortical or compact bone. This type of bone makes up the majority of the skeletal mass and is critical for body structure and the ability for animals including humans, to bear weight, because of its density and resistance to bending. Contained within the cortical bone is another layer of bone tissue that is spongy or soft, and is known as cancellous bone. Cancellous bone is typically found at the ends of long bones, for example, close to joints. Depending on the type of joints and location, the cartilaginous layer that protects the ends of long bones may vary in thickness, as will the thickness of the cortical and/or cancellous bone layers. The implants that are described in greater detail below are readily configurable to account for a wide variety of thicknesses of any of these layers of tissue.

Generally speaking, the region of tissue to be repaired is cartilage that overlays the surface of the tissue, wherein a sub area of that cartilage is damaged or diseased and abuts a region of healthy or non-damaged cartilage tissue (the region to be repaired or replaced referred to as the treatment region).

There are many different potential causes for damaged cartilage tissue. Mechanical or physical causes (such as trauma) are common, as our overuse type injuries. Moreover, a variety of diseases can negatively impact cartilaginous tissue. Some of the major causes of damage or diseased cartilaginous tissue include, obesity (mechanical and/or biochemical), trauma, joint instability, nutritional deficits, medication, hormonal changes, poor biomechanics, and age. Chondrodystrophies are a group of diseases that disrupt growth and/or ossification of cartilage. Some common diseases that affect the cartilage include osteoarthritis (which is a disease of the whole joint, however one of the most affected tissues is the articular cartilage), achondroplasia (reduced proliferation of chondrocytes, relapsing polychondritis (autoimmune destruction of cartilage), tumors and the like.

In view of the variety of potential causes of damage the cartilaginous tissue, or disease of such tissue, there is a need for implants that can promote the repair and/or regeneration of such tissue. Provided for herein are implants configured to achieve those goals of facilitating repair and/or regeneration of soft tissue such as cartilage.

Joint Types

A joint is a connection of the ends of bones in which they interact with one another. There are several types of joints in the human body. Joints can be characterized by its composition or material, the most common type being synovial joints. Synovial joints are joints in which the surface of the bones are covered in articular cartilage and synovial fluid. There are several types of synovial joints, including gliding joints, hinge joints, and ball and socket joints. The knee joint is an example of a synovial hinge joint that can both flex and extend and has limited movement along one axis. The glenoid joint is located in the shoulder and is a synovial ball and socket joint that has a large free range of motion. The joints in the bones of wrists and ankles are synovial gliding joints, which allows for movement in any direction along a single plane. Intrametacarpal joints are synovial gliding joints in the hands between the metacarpal bones. Intermetatarsal joints are synovial gliding joints between the metatarsal bones in the feet. The implants provided for herein are useful for repairing soft tissue in one or more of these various joint types, depending on the embodiment.

Implant Characteristics

Depending on the embodiment, the implant can be made of pyrocarbon, graphite, carbon fiber, titanium, stainless steel, plastic, other polymeric material, or other suitable biocompatible material. Optionally, the implant can further be seeded with growth factors to stimulate cellular growth for cartilage regeneration.

The implant can be used in a variety of ways. In some embodiments, a single implant can be used to repair damaged cartilage within the joint. In other embodiments, a plurality of implants can be used. In some embodiments, multiple implants can be used within a single joint space, conceptually similar to mosaicplasty, wherein a plurality of implants are implanted in a mosaic-like fashion for correction of localized defects.

Anchoring Region

Depending on the embodiment, the implants provided for herein comprise an anchoring region or a specific anchoring structure. As discussed herein, the anchoring region of the implants is in reference to the portion of an implant that is positioned more distally with respect to a joint space (e.g., a first portion of the implant is located closer to a joint space (or in the joint space) as compared to a second portion of the implant that is located more distally). By way of example, FIG. 16C shows a spherical implant according to several embodiments disclosed herein. The stimulating region (discussed more below) is region 102. The anchoring region is depicted as 130. It shall be appreciated that the anchoring region 130 allows for retention of the implant in one or two axes, yet allows for micro-movements of the implant (e.g., movement in limited degrees of freedom (e.g., lateral, linear or rotational movements). Depending on the embodiments, the anchoring region can be fully within the region of cortical bone. However, in some embodiments the anchoring region is at least partially within the cortical bone and partially within the underlying cancellous bone region (e.g., FIGS. 3B and 3C). In still additional embodiments, the anchoring region is configured to lie entirely within the layer of cancellous bone (with the stimulating region, being discussed in more detail below, positioned at least partially within the cortical bone and/or cartilaginous layers).

Depending on the ultimate position into which the implant is placed, e.g. which particular joint space, the anchoring region (and the entirety of the implant, in several embodiments) can be configured such that the dimensions of the implant allow the anchoring region to be positioned within the desired layer, or layers, of bony tissue.

Cap and Stem Implants

Figure 3A:
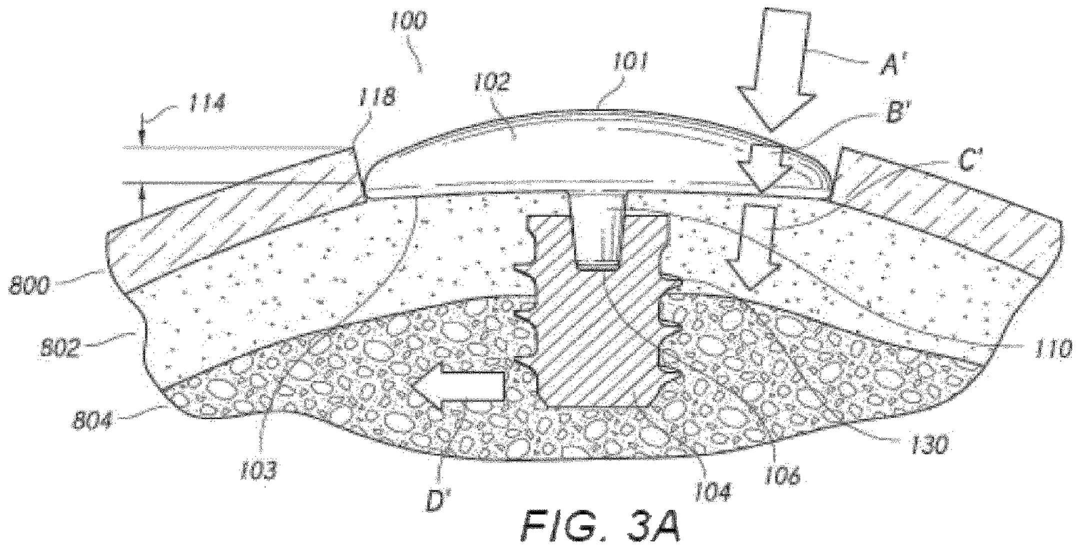
FIGS. 3A-3C illustrate side views of various embodiments of a cap and stem implant with a discontinuity between the surface of the implant and the surrounding cartilage, according to several embodiments disclosed herein.

In several embodiments, the implants disclosed herein can be generally considered as a "cap and stem" variety of implant. For example, such implants may comprise a "cap" region that is positioned within the area of cartilage to be repaired or replaced and a stem region that is configured to be positioned within bony tissue underlying that area of cartilage. In several embodiments, the anchoring region is configured as a multi-part system. FIG. 3A depicts a non-limiting embodiment of such an implant anchoring region 130. By way of example, a permanent bone anchor 104 is inserted and comprises a receiving region 106 into which another component of the anchoring region 130 is inserted or otherwise interacts. In several embodiments, the permanent bone anchor 104 interacts with the additional component of the anchoring region 130 in a reversible manner. In other embodiments, the interaction is intended to be permanent. In several embodiments, the permanent bone anchor 104 comprises one or more features or elements that allow the permanent bone anchor 104 to be securely fitted into a recess in the bony tissue. The permanent bone anchor 104 can be cylindrical, in some embodiments, such as to allow the permanent bone anchor 104 to be threaded into a recess in the bony tissue. Thus, the permanent bone anchor 104 can be threaded, tapered, ribbed, or barbed, depending on the embodiment. In several embodiments, the permanent bone anchor 104 is configured to be adhered to the bony tissue, for example by a biologically compatible adhesive. In several embodiments, the permanent bone anchor 104 is configured to accept, or in some embodiments, promote, in-growth of bone tissue. For example, in several embodiments, the permanent bone anchor 104 comprises a plurality of surface modifications, such as crevasses or through holes, into which bony tissue can grow, thereby securing the implant within the desired area of the bony tissue.

Depending on the embodiment, the permanent bone anchor 104 is configured to sit partially within the cortical bone layer and partially within the cancellous bone layer. In some embodiments, however, the permanent bone anchor 104 is contained entirely within either the cortical or cancellous bone layer. Thus, depending on the embodiment, the height of the permanent bone anchor can range from about 2 mm to about 20 mm, including about 2 to about 4 mm, about 3 to about 5 mm, about 5 to about 7 mm, about 7 to about 10 mm, about 10 to about 13 mm, about 13 to about 15 mm, about 15 to about 18 mm, about 17 to about 20 mm, and any value between those listed, including endpoints.

In some embodiments the permanent bone anchor 104 has a horizontal dimension (e.g., a diameter if a cylinder shape is used) ranging from about 2 mm to about 10 mm, including about 2 to about 4 mm, about 4 to about 6 mm, about 6 to about 8 mm, about 8 to about 10 mm, and any value between those listed, including endpoints.

The shape of the permanent bone anchor 104 can vary, depending on the application (e.g., the joint space), the anticipated load on the joint, and the various thickness of, for example, the cartilage 800, the cortical bone layer 802, and the cancellous bone layer 804. In some embodiments, a cylinder is used. In some such embodiments, the cylinder represents a shaft, which is further threaded, barbed, rubbed, or otherwise shaped with a varied dimension or texture on the outer surface to aid the anchoring into the bone layer(s).

As discussed above, the anchoring region 130 can comprise a stem 110 that is designed to insert into a corresponding receiving region 106 in the permanent bone anchor 104 (see, e.g., FIG. 3A). The stem 110 can vary in dimensions or shape depending on the embodiment. For example, in some embodiments, the stem 110 is a tapered shape, having a cylindrical, rectangular, square or triangular cross section. In several embodiments, the stem 110 comprises a Morse Taper. In additional embodiments, the stem 110 is threaded and threads into a corresponding receiving region 106 in the permanent bone anchor 104. In some embodiments, the stem 110 is fitted with a barb or protrusion that is spring operated and upon insertion of the stem 110 into the corresponding receiving region 106 of the permanent bone anchor 104 expands outwardly into a recess within the receiving region 106 and mates (optionally in a reversible manner) the stem 110 to the permanent bone anchor 104.

The size of the stem 110 and corresponding receiving region 106 can vary, depending on the embodiment. For example, the largest horizontal dimension of the stem 110 and the corresponding receiving region 106 (e.g., a diameter or width) ranges from about 2 mm to about 10 mm, including about 2 to about 4 mm, about 4 to about 6 mm, about 6 to about 8 mm, about 8 to about 10 mm, and any value between those listed, including endpoints.

Similarly, the vertical dimensions of the stem 110 and the corresponding receiving region 106 can vary, based on the joint type or bone that the implant is to be anchored to. For example, an anchoring region that is placed deeper into the underlying bone tissue may be used, for example in relatively larger joint spaces, such as the knee, hip, or shoulder. In contrast, shallower depths may be used in relatively smaller joint spaces, such as the elbows, wrists, metatarsal and metacarpal joints. To that end, the height of the stem 110 and corresponding receiving region 106 can range from about 2 mm to about 15 mm, including about 2 to about 4 mm, about 3 to about 5 mm, about 5 to about 7 mm, about 7 to about 10 mm, about 10 to about 13 mm, about 12 to about 14 mm, about 13 to about 15 mm, about 15 mm to about 18 mm, about 18 mm to about 20 mm, and any value between those listed, including endpoints.

Figure 3B:
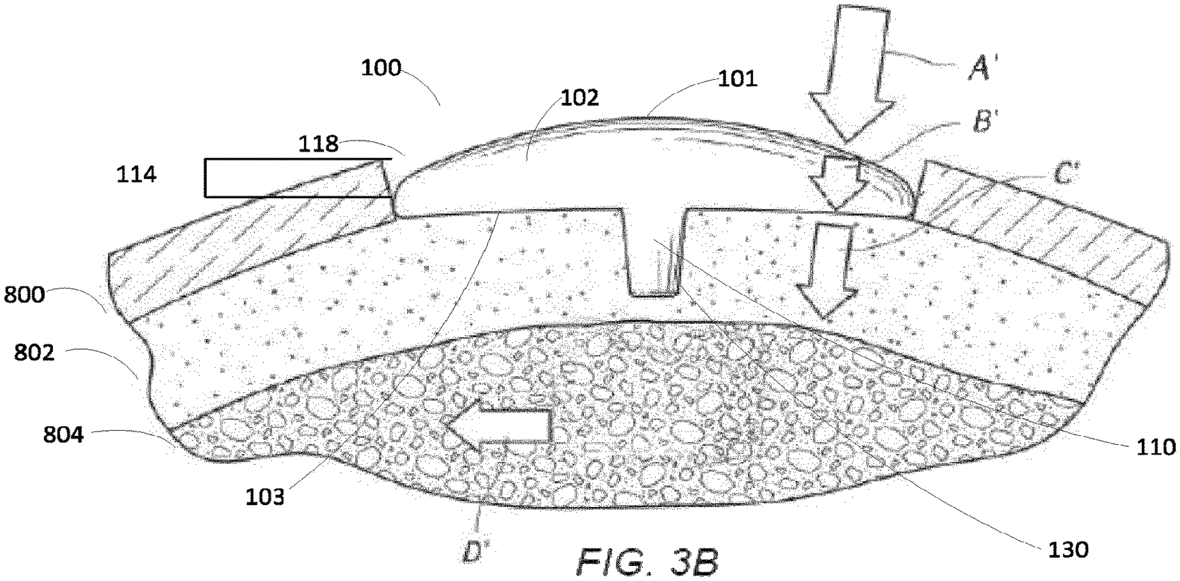

In some embodiments, the anchoring region 130 can comprise a threaded structure or stem 110, similar to the shaft of a screw, which threads into the bony tissue underlying the damage region of cartilage and also interacts with the stimulating region of the implant (discussed more below). The anchoring region 130 can be positioned within the cortical bone layer 802 only. FIG. 3B provides a non-limiting example of such an implant. The anchoring region 130 can also be positioned partially within the cortical bone layer 802 and partially within the cancellous bone layer 804. FIG. 3B provides a non-limiting example of such an implant. The stem 110 can be cylindrical, in some embodiments and can be smooth, tapered, ribbed, or barbed, depending on the embodiment. Any types of variation in surface dimensions or structure that change the degree of friction of the implant stem 110 against the bony tissue may be used, for example, circumferential rings of varying size encircling the stem (perpendicular to the long axis of the stem), threads, grooves, changes in texture, dimples, pores or other through-holes, etc.

Figure 3C:
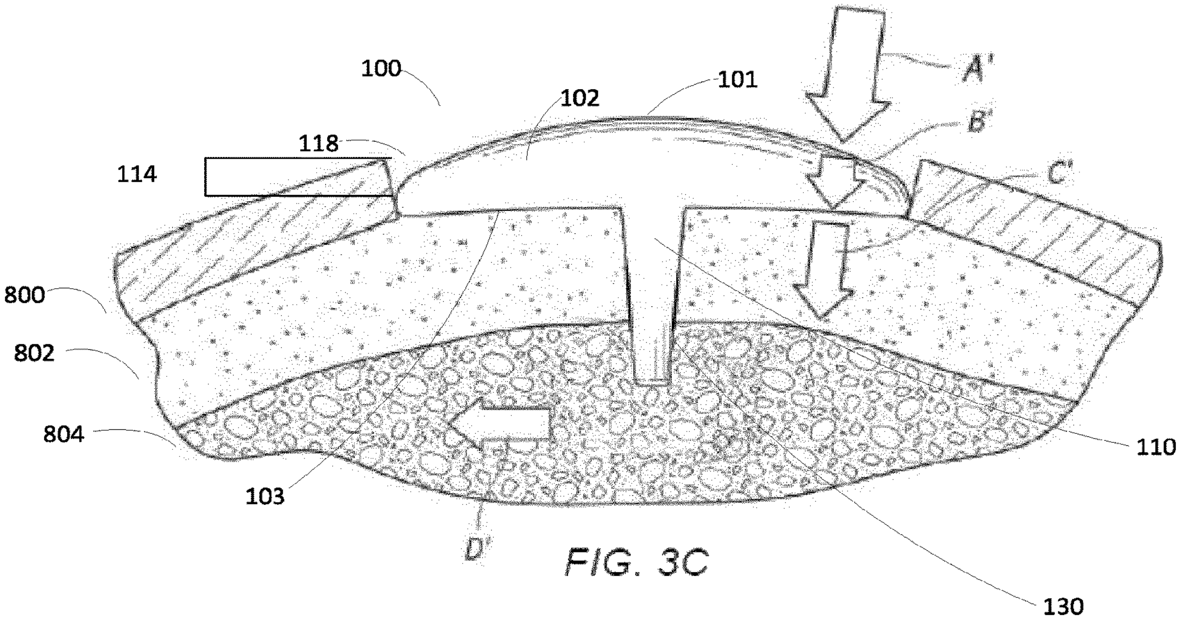

An anchoring region 130 can comprise a stem 110 that may extend from the concave lower face 115 in the vertical direction away from the cap 101. In such embodiments, the stem 110 may be generally conical along its entire vertical length. In a still further embodiment, the overall vertical length of the stem 110 may be at least 50% of the diameter of the cap 101. In some embodiments the stem 110 is a unitary portion of the implant (e.g., is one-piece). By way of non-limiting example, FIGS. 3A-3C depict implants with a unitary implant cap and stem. In additional embodiments, multipart implants can also be used.

In several embodiments, the stem 110 has a cylindrical portion extending from the lower face 103 in the vertical direction away from the concave upper face 101, and a conical portion further extending from the end of the cylindrical portion in the vertical direction away from the cap 101. The cylindrical portion may be of any length and may have a length along its vertical axis of from about one millimeter to about 5 millimeters, alternatively from about 2 millimeters to about 3 millimeters. Without wishing to be bound by the theory, in several embodiments the cylindrical portion is preferable as it allows for ease of manufacturing, e.g., it provides a physical structure to clamp during manufacturing.

The conical portion may be of any length and preferably ranges along its vertical length from about 2 millimeters to about 15 millimeters, including about 2 to about 4 mm, about 4 to about 6 mm, about 6 to about 8 mm, about 8 to about 10 mm, about 10 to about 12 mm, about 12 to about 14 mm or about 13 to about 15 mm, and any length therebetween, including endpoints. In several embodiments, the maximum circular radius of the conical portion may be located at the intersection between the conical portion and the cylindrical portion, and is equal to the circular radius of the cylindrical portion. The conical portion may have radii that decreases from the maximum to a minimum along its vertical axis in the direction away from the cap 101. The circular radii of the conical portion may be of any length, and may range from about 1 millimeter to about 5 millimeters, including about 1 to about 2 mm, about 2 to about 3 mm, about 3 to about 4 mm, about 4 to about 5 mm, and any radii therebetween, including endpoints.

With respect to FIG. 3A, the conical portion may have circumferential grooves around its perimeter. The shape of the circumferential grooves may be defined by a partial torus having a tubular radius of any length, and may range from about 0.25 millimeters to about 2 millimeters, including about 0.25 to about 0.5 mm, about 0.5 to about 0.75 mm, about 0.75 to about 1 mm, about 1 to about 1.5 mm, about 1.5 to about 2 mm, and any length therebetween, including endpoints. The circumferential grooves may be spaced apart at any distance, and may be spaced apart at a distance from about 1 to about 3 millimeters from each other along the vertical, alternatively from about 2 to about 2.5 millimeters.

In several embodiments, the stem 110 comprises a Morse taper, ranging in vertical length from about 2 millimeters to about 15 millimeters, including about 2 to about 4 mm, about 4 to about 6 mm, about 6 to about 8 mm, about 8 to about 10 mm, about 10 to about 12 mm, about 12 to about 15 mm and any length therebetween, including endpoints. The diameter of the Morse taper can range from 1 millimeter to about 10 millimeters, including about 1 to about 2 mm, about 2 to about 3 mm, about 3 to about 4 mm, about 4 to about 5 mm, about 5 to about 6 mm, about 6 to about 7 mm, about 7 to about 8 mm, about 8 to about 9 mm, about 9 to about 10 mm, and any diameter therebetween, including endpoints listed.

In several embodiments, the cap 101 comprises a half spherical portion having an upper convex portion positioned within the area of cartilage to be repaired or replaced. The cap 101 comprises an approximately flat or, alternatively, concave lower surface 103 that rests on the underlying cortical bone layer 802. In some embodiments, the cap 101 has a fillet radius of from about 0.1 millimeters to about 1.5 millimeters, including about 0.1 to about 0.3 mm, about 0.3 to about 0.5 mm, about 0.5 to about 0.7 mm, about 0.7 to about 1.0 mm, about 1.0 to about 1.2 mm, about 1.2 to about 1.5 mm, and any radius between those listed (including endpoints). In several embodiments, the fillet radius comprises a rounded edge that is positioned at the margin 118, where the implant and layer of healthy cartilage are juxtaposed.

Stimulating Region

FIG. 1 shows an implant 700 according to the prior art. Of particular note is the intersection between the upper portion of the implant 702 with the surrounding tissue 800, the margin shown as 118, which is a smooth transition as a result of the configuration of the prior art implant. Such implants are designed to precisely align the surface of the implant with the contours of a particular patient's defect in cartilage. That precise alignment results in regeneration of a smooth and continuous joint surface. These implants presented certain advantages for both patient and surgeon. For example, the patient receiving such an implant reported significant range of motion improvement and rapid recovery times, as well as reduced joint pain. For surgeons, these implants presented a procedure that could be replicated across multiple joints. The procedure also preserved normal joint mechanics and preserved the ability to undertake future procedures, such as total joint replacement.

Such implants, in contrast to those disclosed herein, have several downsides. The custom configuration for an individual patient requires additional time and effort to generate the implant and/or required shaping or configuring implants in the operating suite. This requires additional lead time to prepare an implant as well as potentially requiring more than one procedure (e.g., a first to take measurements and determine the dimensions of the cartilaginous defect and a second to actually place the implant). Additionally, if on-site shaping/customization was undertaken, numerous "blanks" are required to provide the surgeon with a "best-fit" starting implant. However, even with this on hand, the fitting and shaping lengthens the implantation procedure.

Figure 2:
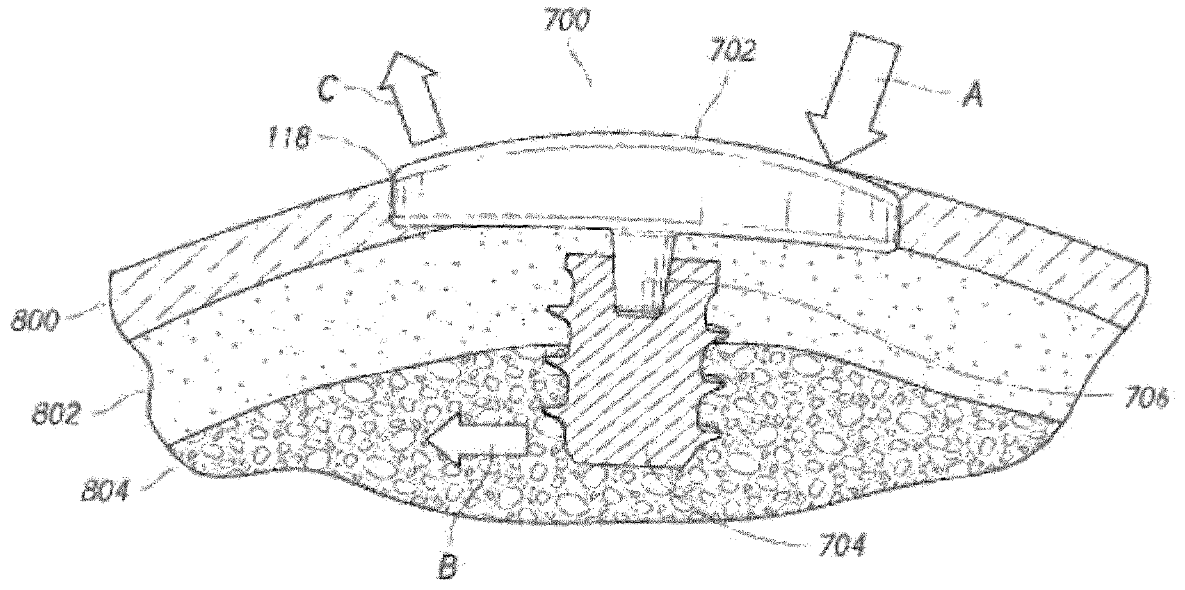
FIG. 2 (Prior Art)
FIG. 2 illustrates a side view of a prior art cap and stem implant with a linear force applied on the implant.

Moreover, as shown schematically in the prior art implant of FIG. 2, the precise alignment that is desirable can in itself create a misalignment between the implant and the surrounding cartilage. For example, a linear force (A) (such as that caused by normal use of the joint) that is placed on one region of the upper portion of the implant 702 can also act as a rotation-inducing force on the implant. This rotational force can impart a lateral force (B) on the anchor of the implant 704. This lateral force causes a lateral displacement of the anchor of the implant 704. Because of the rigid nature of the implant, the lateral displacement (B) of the anchor in turn results in an upward displacement (C) of the upper portion of the implant 702 in a direction generally opposite to that of the originally applied force (A). An analogous example is that if one pushes downward on one side of a dinner plate, the opposite side of the plate will be lifted off the table. The upward displacement (C) of the upper portion of the implant 702 essentially recreates a defect in the cartilage either on the implant-bearing side of the joint and/or on the cartilage of the opposing portion of the joint and thus re-introduces many of the problems that the implant was intended to correct in the first place.

In joints where force (A) is alternately applied, for example at a right side of the implant as schematically shown in the prior art implant of FIG. 2, followed by application of force (A) on the left side of the implant (the reverse of that shown), the anchor of the implant 704 can become loose or dislodged due to the repeated opposing lateral forces (B and opposite of B). This can exacerbate the problems with the implant misalignment because the implant is now is placed in a recess in the bone that is larger than ideal for stable implant retention, meaning that the desired precise alignment of the upper portion of the implant 702 and the surrounding cartilage 800 is even less probable.

The present disclosure provides for implants that address the problems discussed above and also provide an added benefit of regeneration of cartilaginous tissue. The implants disclosed herein provide these benefits, at least in part, based on their dimensions and materials, and the resulting environment that is created at the margin of the cartilage where the implant and the native cartilage interact. In several embodiments, the implants are dimensioned to create a discontinuity between the surface of the implant and the surrounding cartilage. These discontinuities are either step-ups or step-downs (or combinations thereof), depending on the embodiment.

The implants provided for herein may be unitary (e.g., one piece) or may be a multicomponent implant. Regardless of the type of implant, the implant comprises a stimulating region, which functions to stimulate the regrowth/regeneration of cartilage tissue, in order to at least partially replace damaged or diseased soft tissue, such as cartilage. As mentioned above, the implants provided for herein are dimensioned to generate a discontinuity between the implant and the surrounding cartilage, whether being a step-up or step-down discontinuity.

FIG. 3A-C schematically depict an implant 100 according to several embodiments disclosed herein. The implant 100 comprises a stimulating region 102 that is positioned, at least in part, within a layer of cartilage 800. The thickness of the layer of cartilage 800, and thus the stimulating region 102 can vary, depending on the joint space the implant is configured to be implanted in. For example, cartilage thickness is likely to be larger in a weight bearing articulating joint such as the knee, as compared to, for example, an intrametacarpal joint. In some embodiments, the stimulating region 102 comprises an upper surface 101 and a lower surface 103. In several embodiments, the upper surface is positioned to be facing an opposing side of a joint space. In general, the stimulating region comprises an arcuate shape. This is schematically shown in FIG. 3, where the upper surface 101 is a curved shape with rounded edges that blend into the lower surface 103, the lower surface 103 configured to sit on a layer of tissue. In some embodiments, the lower surface 103 sits on a layer of cartilage 800 that is thinner than then surrounding area. In some embodiments, the lower surface 103 sits within the cartilage layer, but rests on the underlying cortical bone 802, which sits above a region of cancellous bone 804.

FIGS. 3B and 3C schematically depicts an implant 100 without a bone anchor 704. The implant 100 comprises a stimulating region 102 and a stem 110 which can be positioned directly within the cartilage layer 800, the cortical bone layer 802, and/or the cancellous bone layer 804 without a bone anchor 704. The stem 110 can be positioned within the underlying cortical bone 802 as shown in FIG. 3B. The stem can also be positioned partially within the cortical bone region 802 and partially within the cancellous bone region 804 as shown in FIG. 3C. This can place the implant 100 in contact with the surrounding tissue, which facilitates the formation of cartilage and/or bone regeneration, as discussed more below.

The stimulating region of the implant can vary in shape when looked on from and end-on perspective. The implants can be square, ovalized, triangular, or generally circular. In some embodiments, discussed in more detail below, the implant is generally spherical (see, e.g., FIGS. 5-6 and 14-16).

As depicted schematically in FIG. 3A-3C, the margin 118 is the area where the implant and layer of healthy cartilage meet (though not in a smooth continuous line, as is intended for the implants disclosed herein). In several embodiments, the implant 100 is configured such that there is a discontinuity between the implant 100 and the layer of cartilage 800 so that the surface of the implant does not align with the contours of the particular patient's defect in cartilage, as shown in FIG. 3A-3C (which is in contrast to implants of the prior art). A step down discontinuity with a height 114 occurs, in certain embodiments, where the height of the implant 100 is less than the depth of the layer of the cartilage at the margin 118, as shown in FIG. 3. This height 114 of the step down discontinuity can range from between about 0.05 to about 5 mm (including about 0.05 to about 0.075 mm, about 0.075 to about 0.1 mm, about 0.1 to about 0.3 mm, about 0.3 to about 0.5 mm, about 0.5 to about 0.75 mm, about 0.75 to about 1 mm, about 1 to about 1.5 mm, about 1.5 to about 2 mm, about 2 to about 2.5 mm, about 2.5 to about 3 mm, about 3 mm to about 3.5 mm, about 3.5 mm to about 4.0 mm, about 4.0 mm to about 4.5 mm, about 4.5 mm to about 5.0 mm, and any height therebetween, including endpoints), as measured from the upper surface of the implant 100 at the margin 118 to the upper surface of the cartilage layer 800.

Figure 16A:
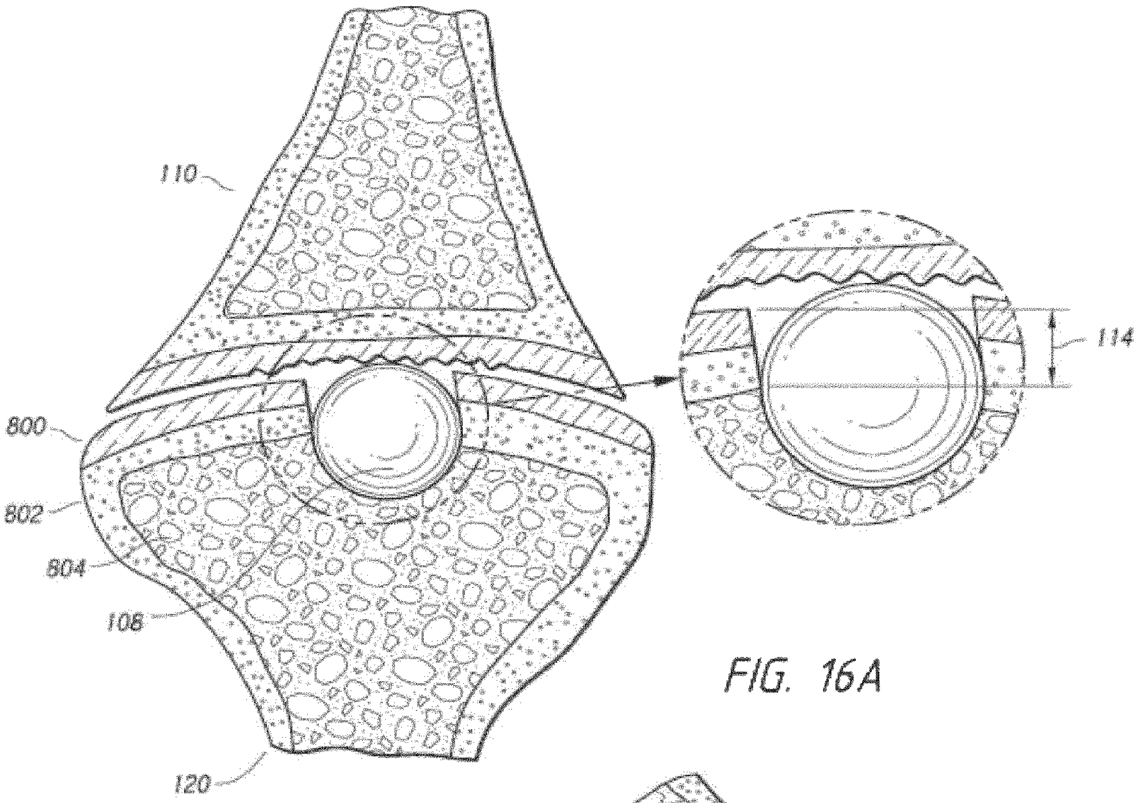
FIG. 16A illustrates a side view of a spherical implant in a joint with damage on the opposing joint surface and an enlarged view of the margin between the implant and the recess into which the implant is placed.
Figure 16B:
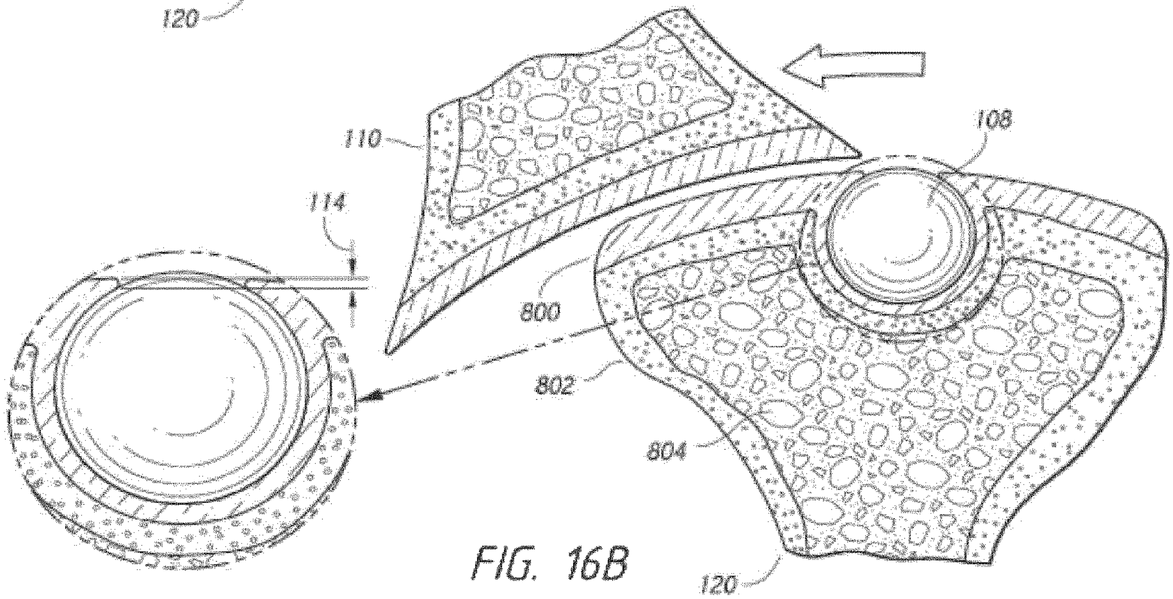
FIG. 16B illustrates a side view of a spherical implant with regenerated cartilage and cortical bone and an enlarged view of the margin between the implant and the recess into which the implant is placed demonstrating growth of new cartilage at the margin that aids in retaining the implant in the recess into which it is placed.
Figure 16C:
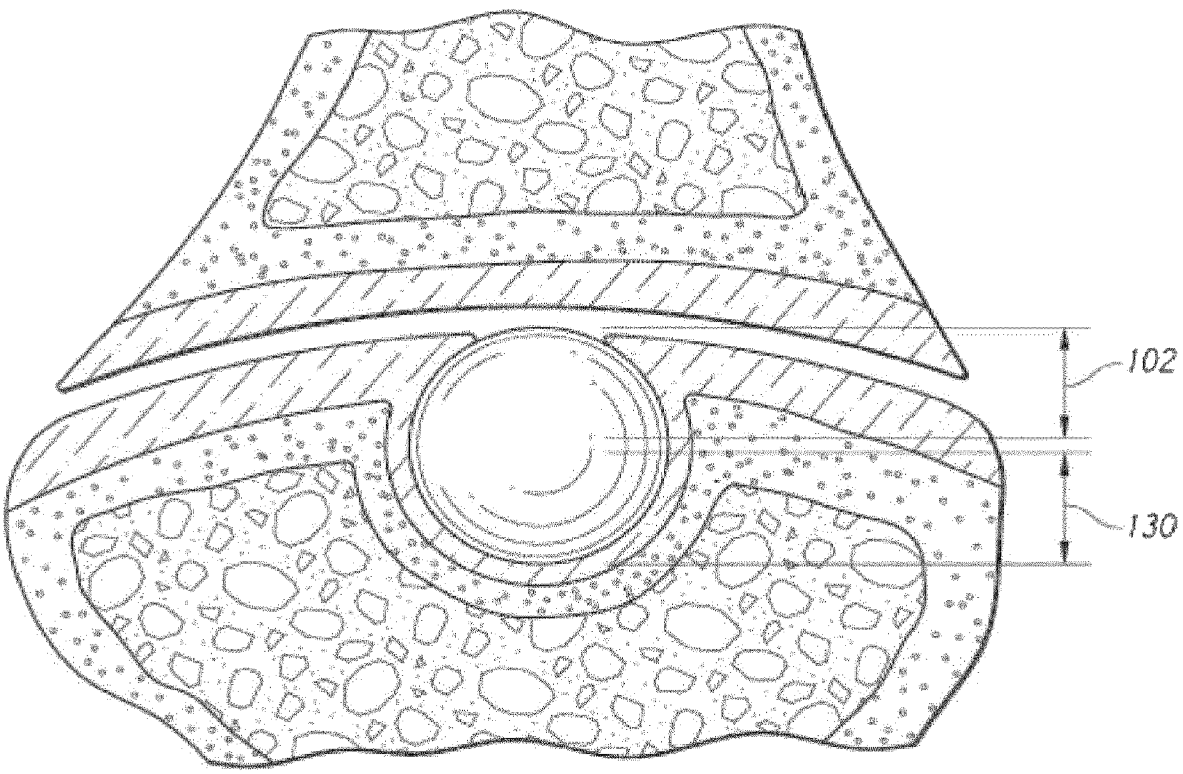
FIG. 16C illustrates a side view of a spherical implant and indicates the relative position of the stimulating region (proximal to the joint space) and anchoring region (distal to the joint space). As discussed herein, the anchoring region does not require complete fixation, but allows at least for some movement (e.g., micro-movement) of the implant.

A step up discontinuity occurs wherein the height of the implant 100 is greater than the depth of the layer of cartilage at the margin (this is depicted schematically in FIGS. 16A and 16B). This height 114 of the step up discontinuity can range from between about 0.05 to about 5 mm (including about 0.05 to about 0.075 mm, about 0.075 to about 0.1 mm, about 0.1 to about 0.3 mm, about 0.3 to about 0.5 mm, about 0.5 to about 0.75 mm, about 0.75 to about 1 mm, about 1 to about 1.5 mm, about 1.5 to about 2 mm, about 2 to about 2.5 mm, about 2.5 to about 3 mm, about 3 mm to about 3.5 mm, about 3.5 mm to about 4.0 mm, about 4.0 mm to about 4.5 mm, about 4.5 mm to about 5.0 mm, and any height therebetween, including endpoints) as measured from the surface of the cartilage layer 800 to the upper surface of the implant 100 at the margin 118.

This lack of precise alignment can be advantageous in the implantation process because it requires less customization and less time in fitting and shaping the implant.

The discontinuity at the margin 118 is desirable because there is a lessened risk to create misalignment between the implant 100 and the surrounding cartilage 800. For example, as shown in FIG. 3A, a linear force (A') that is placed in a region of the upper portion of the implant can result in a transferred linear force (B') applied on the surface of the cortical bone layer. This linear force (B') can be absorbed by the cortical bone layer 802 as linear force (C'). The linear force (A') can still be a rotation inducing force that translates into a lateral force (D') on the anchoring region and an upward displacement on the upper portion of the implant. However, the discontinuity reduces the lateral forces and does not result in a vertical displacement of the implant, according to some embodiments.

When there is a step down discontinuity, the linear forces on the implant do not directly impact the outer perimeter of the implant. Linear forces only make direct contact more towards the center of the implant. The height of the cartilage layer 800 prevents the linear force (A') making direct contact with the edge of the implant at the margin 118. The force that is more centered will result in less torque applied to the implant and better transmission of linear force (O') to the bony tissue layers beneath the implant. This will decrease the risk of misalignment of the implant.

Moreover, the discontinuity of the surfaces can result in shear forces between the stimulating region and the cartilage. The shear forces, in conjunction with the load of the bone on the implant as well as the articular fluids (e.g., synovial liquid and/or blood) can stimulate formation of fibrous tissue, the process being described in more detail below. The fibrous tissue can transform to articular cartilage, thereby facilitating repair and/or regeneration of cartilage.

Spherical Implants

In several embodiments, the implants disclosed herein can be generally considered as a spherical variety of implant. It shall be appreciated that, as such, either hemisphere that makes up the spherical implant can be considered an anchoring region or a stimulating region, depending on the orientation of the implant. In fact, in several embodiments, the implant is dimensioned to allow two dimensional movements within a recess generated to receive the implant. For example, the spherical implant can rotate in "side to side" and "top to bottom" directions within the recess, but not in a significant linear motion back out of the recess. The implant can be retained in a desired location by pressure from the opposing portion of the joint. The implant can also be retained in the implant by a spherical recess with an opening having a diameter less than the diameter of the implant. This can be configured by means of creating a recess with an opening with a smaller diameter. This can also be configured by means of creating a square edged recess, in some embodiments. The square edged recess can stimulate the regeneration of cartilage such that the square edged opening can become smaller with the regeneration of the cartilage.

Figure 4A:
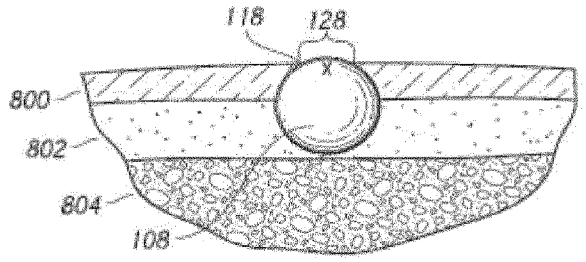
FIGS. 4A-4B illustrate side views of a spherical implant in the cartilage layer and cortical bone layer. These figures also demonstrate that the spherical implant is mobile within the recess formed (e.g., capable of micro-movements and/or rotation).
Figure 4B:
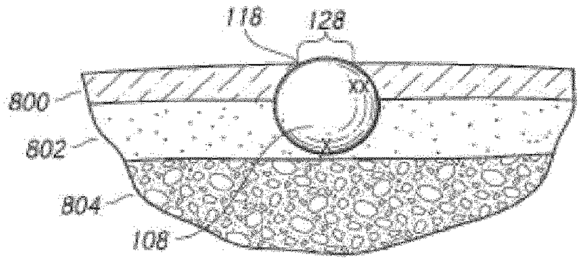
Figure 5:
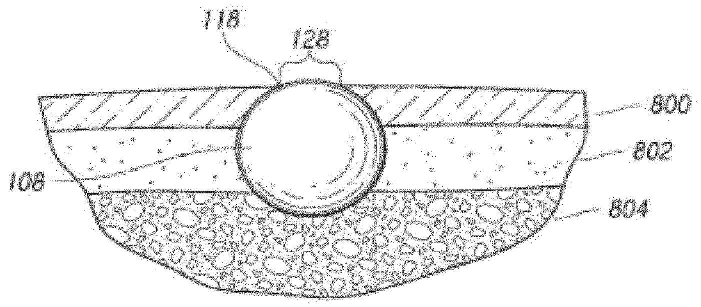
FIG. 5 illustrates a side view of a spherical implant in the cartilage layer, cortical bone layer, and the cancellous bone layer.

FIGS. 4 and 5 schematically depict an implant 108. The implant 108 comprises a stimulating region that is positioned, at least partially, within a layer of cartilage 800 and the underlying cortical bone 802. It shall be appreciated that for such implants, there is the possibility of movement of the implant within the recess, such that a portion that is initially within the bony layer can move such that the portion can later be positioned outside the bony layer (e.g., in the cartilage layer). In other words, an implant positioned with a "marker" region initially at 12 o'clock as labelled "x" as shown in FIG. 4A can rotate such that the marker region is later positioned at 6 o'clock as shown in FIG. 4B. The "marker" region may rotate to other positions at 3 o'clock, 7 o'clock, 9 o'clock, etc. Also depicted in FIG. 4B is position "XX", which reflects that, according to some embodiments, the spherical implant is capable of "micro-movements", conceptually similar to vibration or incomplete rotations. Position "XX" is intended to depict an initial position followed by subsequent micro-movements positioning that point on the spherical implant at "XX".

The thickness of the layer of cartilage 800, and thus the stimulating region can vary, depending on the joint space the implant is configured to be implanted in. For example, cartilage thickness is likely to be larger in a weight bearing articulating joint such as the knee, as compared to, for example, an intrametacarpal joint. The implant 108 can be generally spherical. In general, the stimulating region comprises an arcuate shape.

Figure 6:
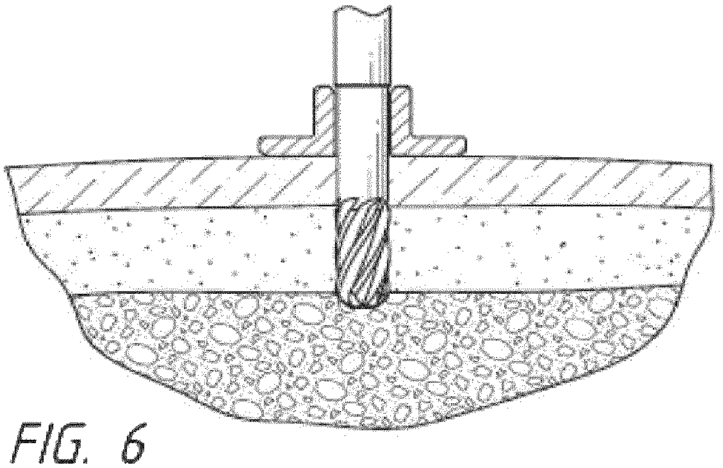
FIG. 6 illustrates a side view of a surgical drill inserted through the cartilage layer and bony tissue.
Figure 7:
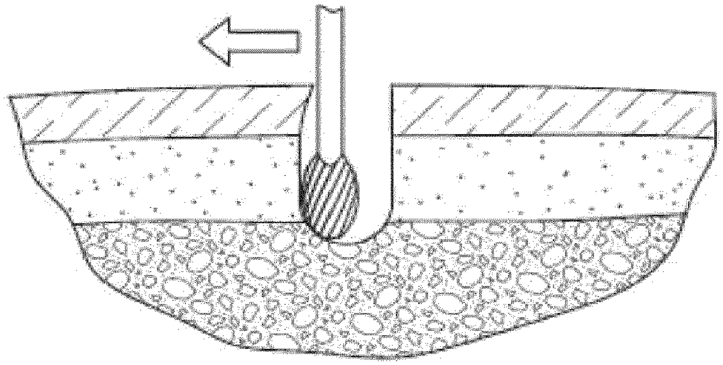
FIG. 7 illustrates a side view of a surgical drill moving in a pattern to form a spherical recess.
Figure 8:
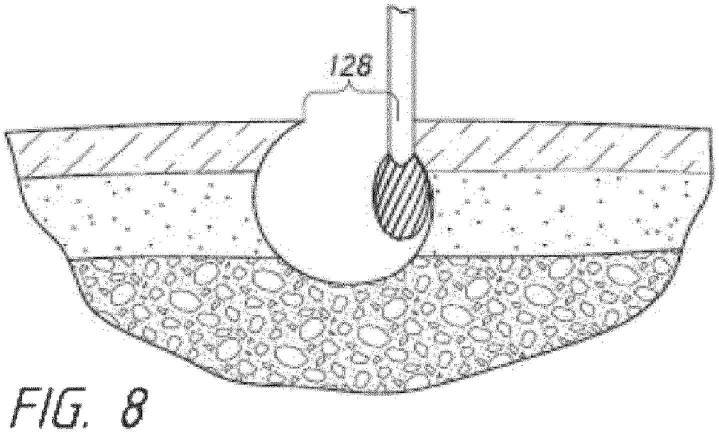
FIG. 8 illustrates a side view of an additional pattern by which a surgical drill can be moved to form a spherical recess.

The surgeon can insert a drill with a depth gage through the cartilage layer 800 into the cortical bone layer 802 as shown in FIG. 6. The drill can further be inserted into the cancellous bone layer 804. The surgeon can then introduce an ovoid burr diameter drill and move it circularly to create a spherical recess. The surgeon can then drill a spherical recessed area as shown in FIGS. 7 and 8.

The recessed area receives the implant 108 and is also generally spherical. The recessed area can extend partially in cartilage layer 800 and partially in the cortical bone layer 802 as shown in FIG. 4. The recessed area can also extend partially into the cancellous bone layer 804 as shown in FIG. 5. Depending on the ultimate position into which the implant is placed, e.g. which particular joint space, the recess can be configured such that the dimensions of the implant allow the implant to be positioned within the desired layer, or layers, of bony tissue.

Figure 9:
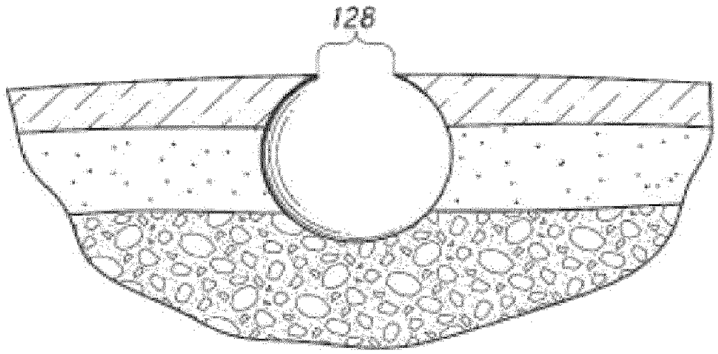
FIG. 9 illustrates a side view of a spherical recess configured to receive a spherical implant.

The diameter of the recessed area can be larger than the diameter of the opening 128 of the recessed area in the cartilage layer as shown in FIG. 9. The diameter of the opening 128 can be 50% to 75% of the outer diameter of the recessed area. The reduced diameter of the opening can help retain the implant within the recessed area.

The size of the spherical implant 108 can vary, depending on the embodiment. For example, the diameter of the spherical implant 108 ranges from about 2 mm to about 10 mm, including about 2 to about 4 mm, about 4 to about 6 mm, about 6 to about 8 mm, about 8 to about 10 mm, and any value between those listed, including endpoints.

Figure 10:
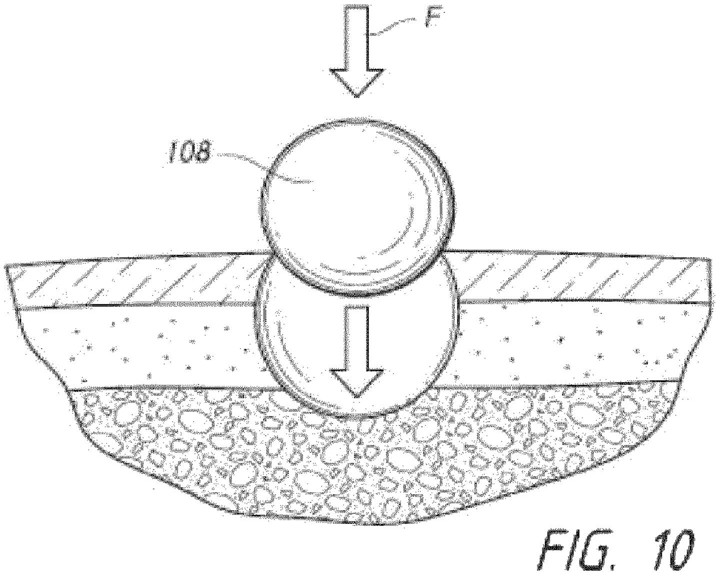
FIG. 10 illustrates a side view of a spherical implant with a linear force applied on the implant.
Figure 11:
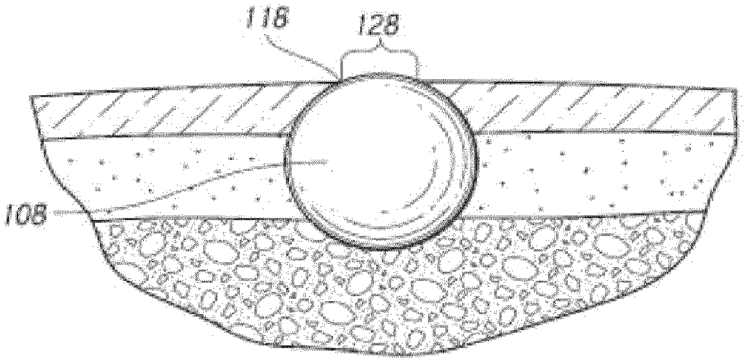
FIG. 11 illustrates a side view of a spherical implant.
Figure 12:
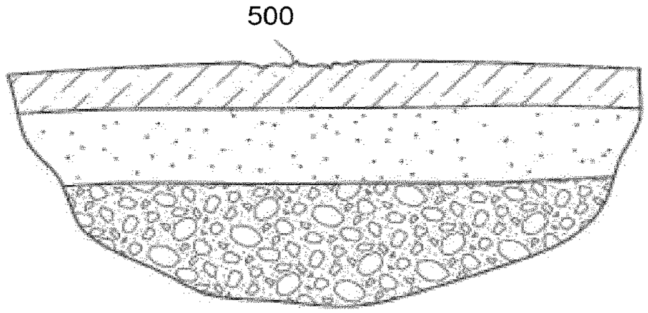
FIG. 12 illustrates a damaged cartilage region.

The implant 108 is inserted into the recessed area with the application of a linear force (F), as shown in FIG. 10. As shown in FIG. 11, the implant 108 is then placed within the recessed area wherein the implant is free to move in two dimensions. Linear and lateral forces applied to the implant can act as rotation inducing force on the implant. This rotational force will cause the implant 108 to rotate within the recessed space because of the shape and rigid nature of the implant. An analogous example is that if a force is applied to a marble, the marble will rotate. Another analogous example is that if a force is applied to a trackball in a mouse, the trackball will rotate in place within the recess of the mouse.

This process can be advantageous because the implant 108 does not require a precise alignment of the surface of the implant with the contours of the particular patient's defect in cartilage. This makes the process faster and less susceptible to error in fit or misalignment.

Additionally, linear or lateral forces that are placed on the implant 108 is less likely to cause misalignment because the implant is spherical. Linear and lateral forces can act as a rotation-inducing force on the implant, such that the implant will rotate within the recessed area, rather than move linearly, as with prior art implants.

The rotational movement can result in shear forces between the stimulating region and the healthy cartilage. This movement and resulting shear force can stimulate the formation of fibrous tissue. The fibrous tissue can transform to articular cartilage, thereby facilitating repair and/or regeneration of cartilage.

Squared Recess

Figure 13:
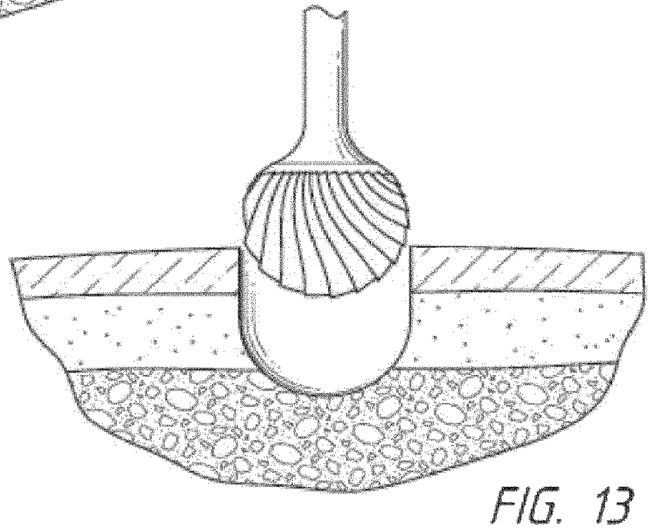
FIG. 13 illustrates a side view of a surgical drill forming a square edged recess.
Figure 14:
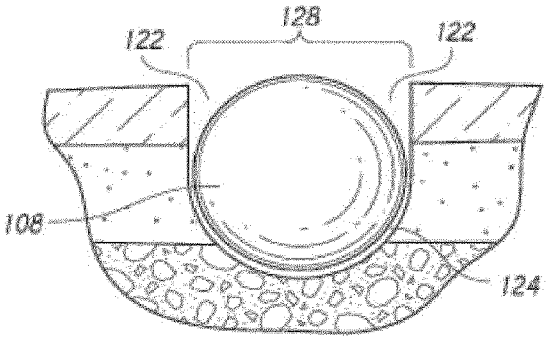
FIG. 14 illustrates a side view of a spherical implant placed within a square edged recess.

In yet another embodiment, the spherical implant can be inserted into a squared edge recess as shown in FIGS. 13 and 14. The square edge recess can be formed such that the diameter of the opening 128 in the cartilage layer 800 and bony tissue layers is be slightly greater (e.g., about 1%, about 2%, about 3%, about 4% about 5%, about 10%) than that implant (thereby allowing for movement of the implant and application of shear forces to the cells within the fluid, thereby stimulating deposition of fibrous tissue. The square edge recess is also advantageous because it can be used to repair an increased amount of damaged cartilage with a smaller sized spherical implant because the diameter of the opening can be the same size as the diameter of the spherical implant. The spherical implant 108 can be retained by the pressure from the opposing portion of the joint as shown by way of example in FIGS. 16A and 16B. The spherical implant 108 can be positioned such that there is a step-down discontinuity having a height 114 such that the load of the opposing portion of the joint 110 can be placed on the implant 108. With the continued load and regeneration of cartilage, the implant 108 will align with the surface of the implanted bone 120 such that the load will be spread between the surface of the implant 108 and surface of the implanted bone 120, with the step-down discontinuity having a height 114 being replaced by a step-up discontinuity having a height 114 when measured at the margin of the recess formed (e.g., the "gap" shown in FIG. 16A). The load of the opposing portion of the joint 110 on the implant 108 can induce movement (e.g., micromovements) of the implant 108. The movement of the implant 108 can stimulate regeneration of cartilage, as discussed more below. The load can be spread on the cartilage and the spherical implant 108 so the implant 108 stays in place within the recess.

Figure 15:
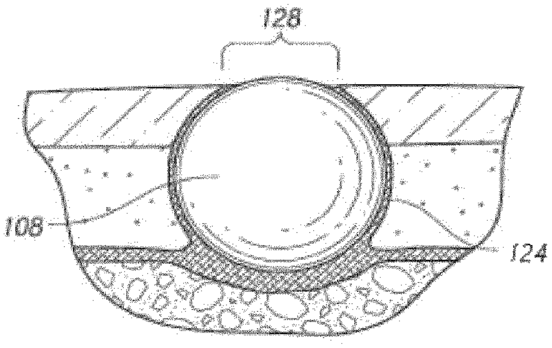
FIG. 15 illustrates a side view of a spherical implant with a cartilage regeneration-inducing fluid layer surrounding the implant.

The square edge recess can be advantageous because the optimal shape of the recess. This can be advantageous for both the surgeon and patient because a larger surgical drill can be used for improved speed and ease of application and use. The recess does not have to be shaped with a smaller diameter of the opening 128 at the cartilage layer 800 than the diameter of the recess. This is also advantageous because the implant 108 can be easily placed through the larger opening or square edge recess as shown in FIGS. 14 and 15. The square edged recess can also be advantageous for the patient because it encourages regeneration or repair of the damaged cartilage over time.

Mechanism of Action

In some embodiments, the spherical implant 108 can be placed in approximate juxtaposition with the bony tissue as show in FIG. 14 (e.g., leaving a gap 122 of between about 0.05 to about 2 mm between the spherical implant and the surrounding tissue). This allows fluid comprising stem or other cell types to moving in the gap 122. In several embodiments, the gap 122 allows two dimensional movement of the implant which imparts a shear force (or forces) on the cells within the fluid (e.g., cells within synovial fluid and/or blood). This shear force, and in some embodiments, applied load between the bone and the implant as well as the articular fluids (e.g., synovial liquid and/or blood) stimulates the formation of cartilage. In several embodiments, the pyrocarbon material of the implant further stimulates the deposition of fibrous tissue in the gap 122. In several embodiments, that fibrous tissue gets subsequently converted to cartilage. In several embodiments, the formed fibrous tissue is transformed to articular cartilage (e.g., in the joint space and surrounding the stimulating region of the implant. In several embodiments, the there is also formation of cartilage between the implant and the bone (e.g., sandwiched between the implant and the bony tissue. In several embodiments, cortical bone is also formed under the implant (e.g., a layer of new cartilage and a layer of new bone is formed between the implant and the original bone). See for example, FIGS. 16B and 16C. In several embodiments, the deposition of cartilage also functions to reduce the size of the opening into which the implant is placed, thereby assisting in retaining the implant within the recess (but still allowing micromovements, in several embodiments). This is advantageous in highly articulating joints (see e.g., FIG. 16B) where articulation may at least temporarily remove the load from the opposing side of the joint from the implant.

Over time, this fibrous tissue is transformed to articular cartilage, due at least in part to continued contact with the implant and the movement of the implant and/or continued shear forces on the fibrous tissue. Eventually, in several embodiments, the articular cartilage can also form cortical bone (for example around the base portion of the spherical implant as shown in FIGS. 15 and 16B). It shall also be appreciated that the shear forces can also allow for deposition of fibrous tissue in the region of discontinuity where cap and stem type implants are used. Thus, it shall be appreciated that the implant configuration and the gap/discontinuity induces the deposition of fibrous tissue that will transform into articular cartilage, thereby facilitating repair and/or regeneration of cartilage. The cartilage can thus regenerate around the spherical implant (or around the stimulating region of a cap and stem implant), which will increase the stability of the implant (but not eliminate micromovements), similar to the implant in the recesses shown in FIGS. 9-11. The movement of the implant in contact with fibrous tissue, or in some cases the continued contact alone, stimulates the transformation of the fibrous tissue to articular cartilage. In some embodiments, the implant can be held in place by the fibrous tissue that can later transform into articular cartilage as shown in FIG. 15. In several embodiments, the continued movement of the implant, and the opposing joint surface prevents the cartilage from growing across the top surface of the spherical implant as shown in FIGS. 16A and 16B by a clean division between the cartilage layers on bone 110 and 120.

In some embodiments, the implant can regenerate cartilage and repair damage to the implanted bone 120. In other embodiments, the implant 108 can also regenerate cartilage and repair damage to the opposing joint surface on the opposing bone 110. The diameter of the damage on the opposing joint surface 110 can be a greater or lesser diameter of the implant 108 as shown in FIG. 16A. The movement of the joint can cause the implant 108 to move against the opposing joint surface in multiple directions. More particularly, the non-limiting example in FIG. 16A depicts a region of damage of cartilage on bone 110 that is has a length greater than the diameter of the spherical implant. When an articulation is applied to the joint, the implant will move from its central position of the defect in the cartilage on bone 110 (shown in FIG. 16A) to a more lateral position. Articulation in the opposite direction would bring the implant back to center, then lateral to the other region of defective cartilage. Thus, it is particularly advantageous that, rather than replacing the entirety of a region of cartilage on a bone with an implant that "caps" the bone, a smaller diameter implant can be used to regenerate a comparatively larger region of cartilage.

Applications and Examples

Discussed in greater detail below are various applications of the implants disclosed herein, for example, discussion of particular arrangements of implants within several non-limiting examples of joint spaces. Also provided below a depiction of implantation of an implant according to several embodiments disclosed herein positioned in the first MTP joint of the patient having damaged cartilage surface within the joint.

As discussed above, implants provided for herein can be used in a variety of joint types, including but not limited to, gliding joints (the ankle, wrist, intermetacarpal, and intermetatarsal), hinge joints (the knee), and ball and socket joints (the shoulder and hip).

Figure 17A:
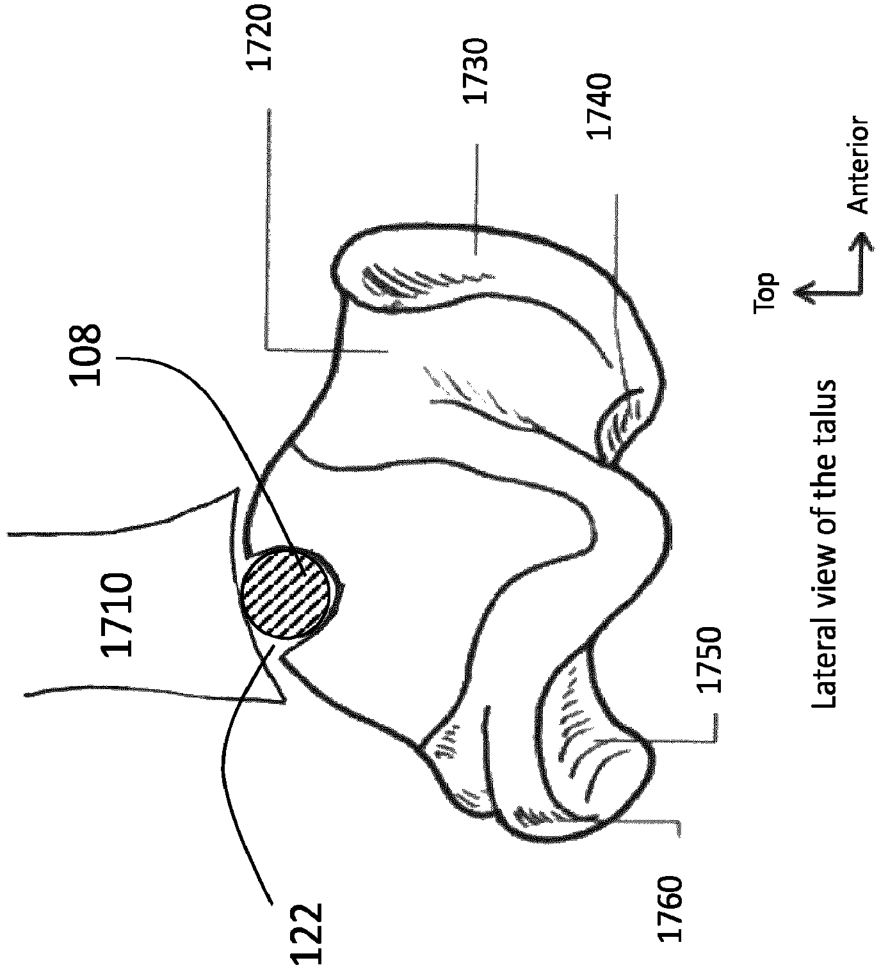
FIG. 17A illustrates a non-limiting embodiment of an implant according to several embodiments disclosed herein wherein the implant is positioned in the talus of the ankle.

FIG. 17A shows one embodiment of an implant 108 positioned for repair of damaged cartilage in the ankle joint. The talar dome 1720 is shown, located above and posterior to the Navicular articular surface 1730. The anterior 1740 and posterior 1750 calcaneal articular surfaces are also shown, as is the lateral tubercle of the posterior process 1760, as anatomical landmarks. As schematically shown, in this embodiment, the implant 108 is positioned in the dome of the talus 1720 such that the implant interacts with the convex surface of the distal portion of the tibia 1710. As discussed in more detail above, the recess in the talus is configured to allow a gap 122 to remain around the implant 108 post-implantation (note that the gap is not shown in every schematic figure, but unless indicated otherwise, it shall be appreciated that the gap is present). Post-implantation, movement of the pyrocarbon implant and load from the bone (here the tibia) will lead to formation of fibrous tissue in the gap. As movement continues, the fibrous tissue will be converted to cartilage. In several embodiments, the lower portion of the recess will be converted from fibrous tissue to cancellous bone (as depicted schematically in FIG. 16A). Based on the defect in the cartilage layer, the implant size is varied to yield a gap between the recess and in the implant that is not overly large. This is apparent to one of ordinary skill in the art, in that, if the arcuate (or spherical) surface of the implant has a radius of curvature that is too small, articulation of the joint in a first direction such that a portion of the opposing joint face moves past the gap will allow that portion of the opposing joint face to "catch" or become "hung up" on the edge of the recess as the joint face returns to its original position. Selection of implant size is therefore done with an aim to initially create a gap that is not overly large, so as to avoid this "catch" and prevent generation of a void that is too large to provide frictional movement between the implant and surrounding bone/tissue and thus fail to result in cartilage regeneration. The implant size is selected such that the initial placement of the implant results in the surface of the implant not being flush with the surrounding cartilage (see, e.g., the step-up discontinuity that occurs wherein the height of the implant is greater than the depth of the layer of cartilage at the margin (depicted schematically in FIGS. 16A and 16B)). In this manner, the implant acts, at least temporarily as a spacer. As time passes, load on the joint, and thus on the sphere, as well as cartilage formation in the gap around the sphere, will lead to a surface that is approximately, if not substantially, flush to the surrounding cartilage layer. One of ordinary skill in the art will also appreciate that implants that are overly large are not desirable, because the two surfaces of an articular surface will not slide over one another, and moreover, preparing a site for implantation of an oversized implant is overly invasive, particularly in certain joints with a relatively thin layer of cancellous bone. In some applications, discussed in more detail below, a large defect size can be treated using a plurality of implants.

Figure 17B:
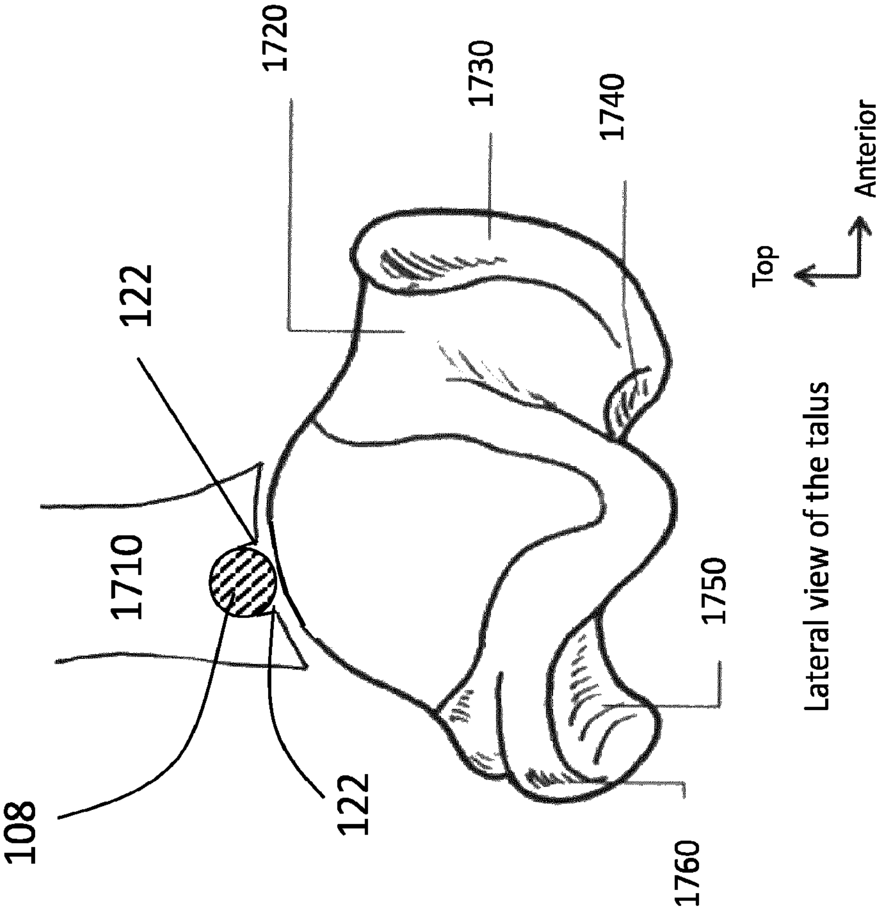
FIG. 17B illustrates a non-limiting embodiment of an implant according to several embodiments disclosed herein wherein the implant is positioned in the tibia, adjacent the talar dome of the ankle.

Moving to FIG. 17B, this schematic depicts an embodiment in which the implant is positioned in the distal portion of the tibia 1710, rather than in the dome of the talus 1720. Depending on the embodiment, the implant can be positioned in the more accessible portion of a given joint, though in several embodiments the implant (or implants) are positioned at the site of the defect. Depending on the embodiment, this may not necessarily be in the center of a joint (see for example FIG. 23D, where the implant is positioned lateral of the centerline of the MTP joint, based on the location of the defect being treated). As will be discussed in more detail below, depending on the embodiment, implants may be positioned on both opposing sides of a joint.

Figure 18A:
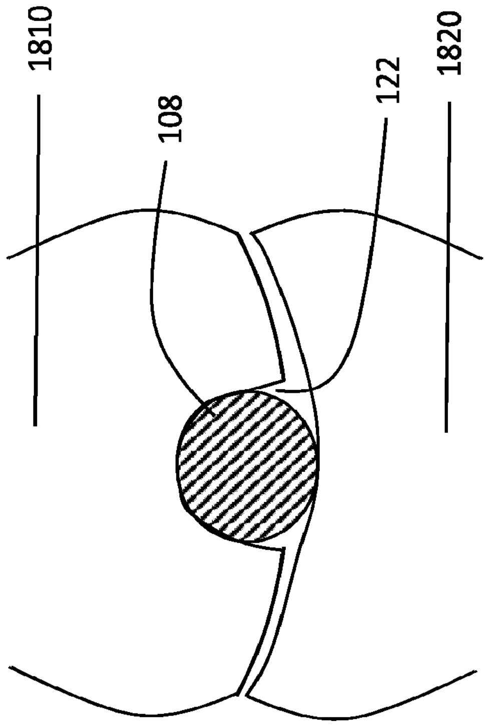
FIG. 18A illustrates a non-limiting embodiment of an implant according to several embodiments disclosed herein wherein the implant is positioned in the knee joint (side view shown).

FIG. 18A depicts a schematic of an implant according to several embodiments disclosed herein positioned in the knee joint. In this schematic side view, a spherical implant 108 is shown positioned in the distal portion of the femur 1810, with associated gap 122 shown on either side of the implant 108. However, according to several embodiments disclosed herein, implants could also be positioned in the proximal portion of the tibia 1820. Likewise, while this schematic shows a single implant, it shall be appreciated that multiple implants can optionally be positioned to treat a plurality of defective cartilage regions and/or treat a single substantially large region of cartilage damage. As discussed above, if an articulating joint is damage on both sides, an implant may optionally be positioned on the side that is easier to access during an implantation procedure. However, as mentioned, other embodiments involve accessing and placing one or more implants on both sides of an articulating joint. Placement of the implant (or implants), particularly in joints with a high degree of articulation, like the knee, can also be driven by the proximity of the defect to a region of the joint that would become exposed upon articulation of the joint. Merely by way of example, if a defect was present on an interior aspect of the distal portion of the femur and an implant was placed at that defect, immediately postoperatively selection of the knee joint would cause the implant to be unopposed (e.g., no longer held in place by the opposite side of the joint) and could present a risk of dislodging of the implant from the recess created to hold it. In several embodiments, therefore restriction of range of motion for a period of 1 to 5 days, 5 to 14 days, 14 to 21 days, or 21 to 40 days, or any number of days there between, facilitates maintenance of the implant in the desired position while fibrous tissue (and ultimately cartilage) fill in the gap 122 around the implant, thus serving to retain the implant in place long-term.

Figure 18B:
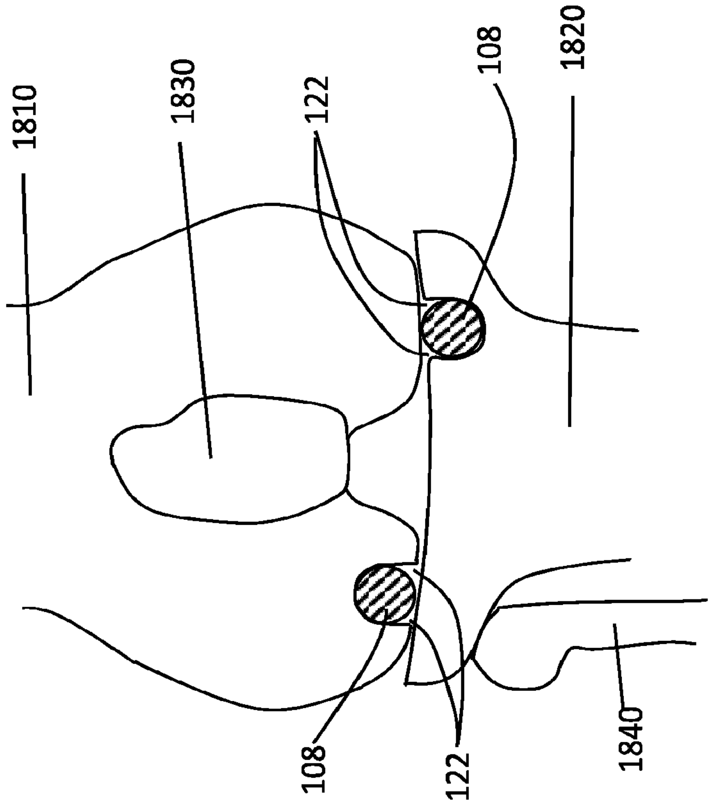
FIG. 18B illustrates a non-limiting embodiment of implants according to several embodiments disclosed herein wherein the implants are positioned in the knee joint (shown implanted in the tibial heads, front view shown).

FIG. 18B depicts another schematic of implants positioned in the knee according to various embodiments disclosed herein. This schematic depicts a front view of the right knee and shows two implants 108, one positioned in a proximal head of the tibia 1820 and the other positioned in a distal portion of the femur 1810. It shall be appreciated that when a plurality of implants are used, they may all be placed on one side of the articulating joint, all on the opposing side of the articulating joint, or a mixture of the two. In some embodiments, the implants are positioned more medially, moving closer to the central portion of joint (closer to the patella 1830). As mentioned above, the placement is driven primarily by the location of the defect and the relative size and/or accessibility of the defect.

Figure 19A:
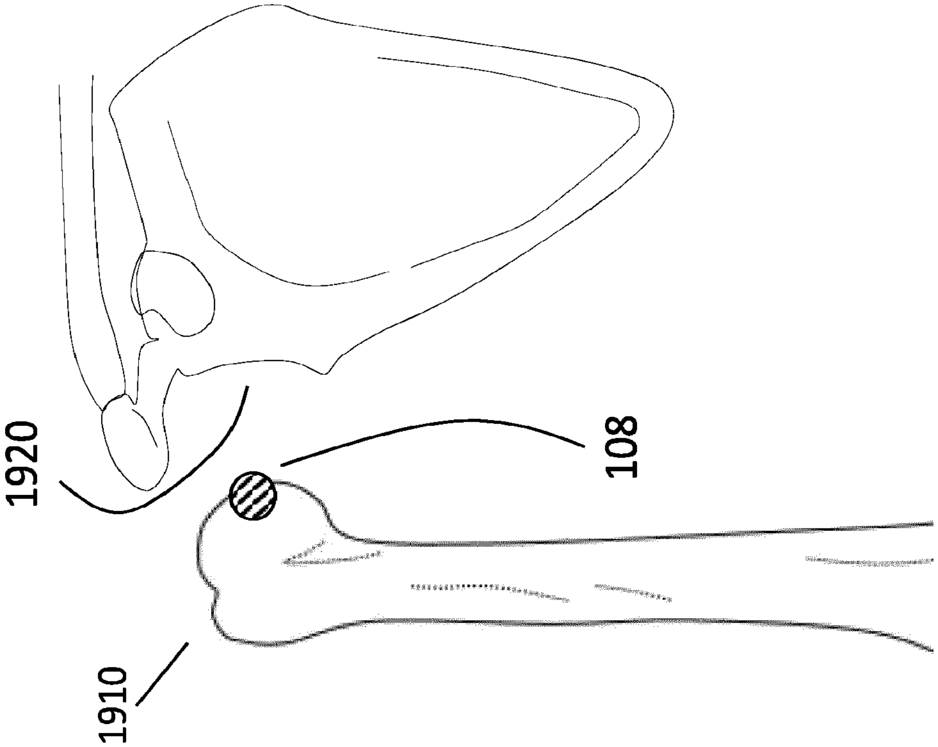
FIG. 19A illustrates a non-limiting embodiment of an implant according to several embodiments disclosed herein wherein the implant is positioned in a convex portion of a joint, such as the head of the humerus at the shoulder.
Figure 19B:
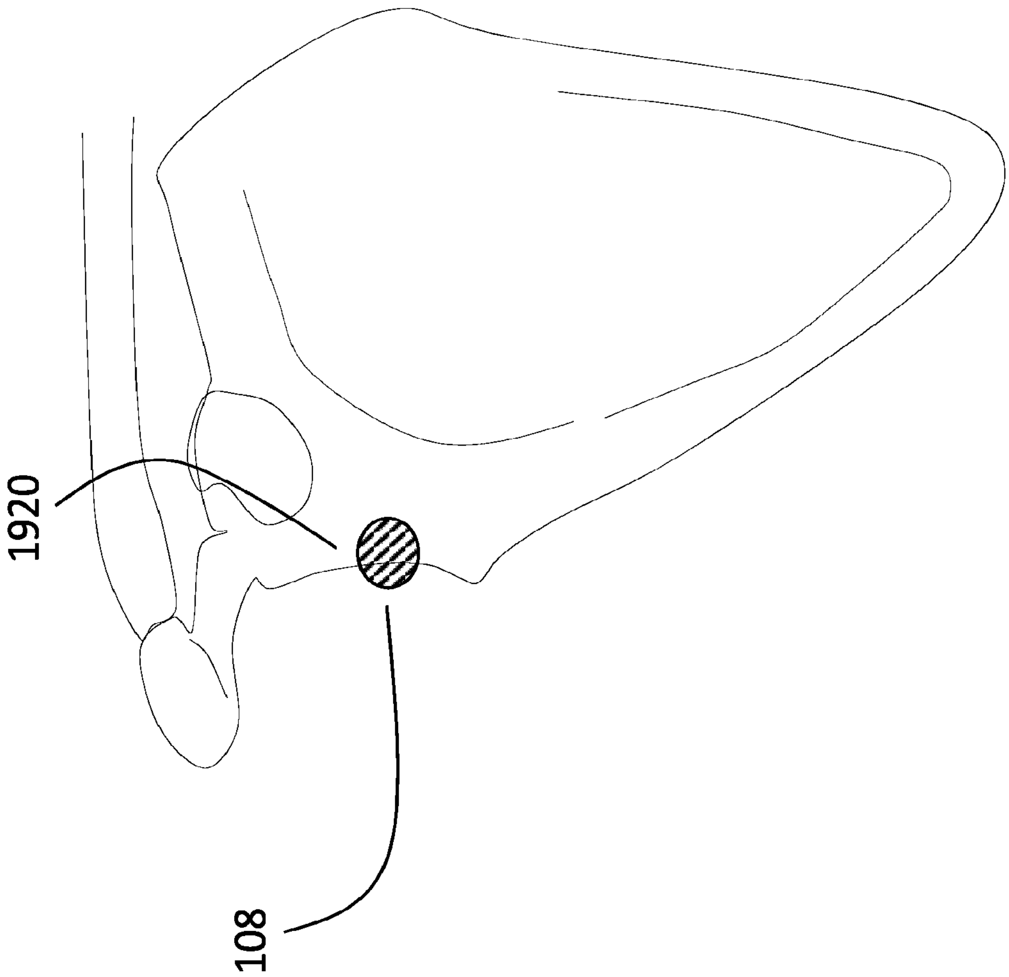
FIG. 19B illustrates a non-limiting embodiment of an implant according to several embodiments disclosed herein wherein the implant is positioned in a concave portion of a joint, such as the glenoid cavity of the shoulder.

Turning to FIG. 19A, this schematic an implant 108 according to several embodiments disclosed herein, where a radius of curvature of the implant 108 does not match the radius of curvature of the opposing joint face. Merely by way of example, FIG. 19A depicts an implant 108 positioned in the head of the humerus 1910 opposing the glenoid cavity 1920 of the shoulder. Alternatively, or in some embodiments, in addition to, an implant 108 could be placed on the concave glenoid cavity 1920 as shown in FIG. 19B.

Figure 20A:
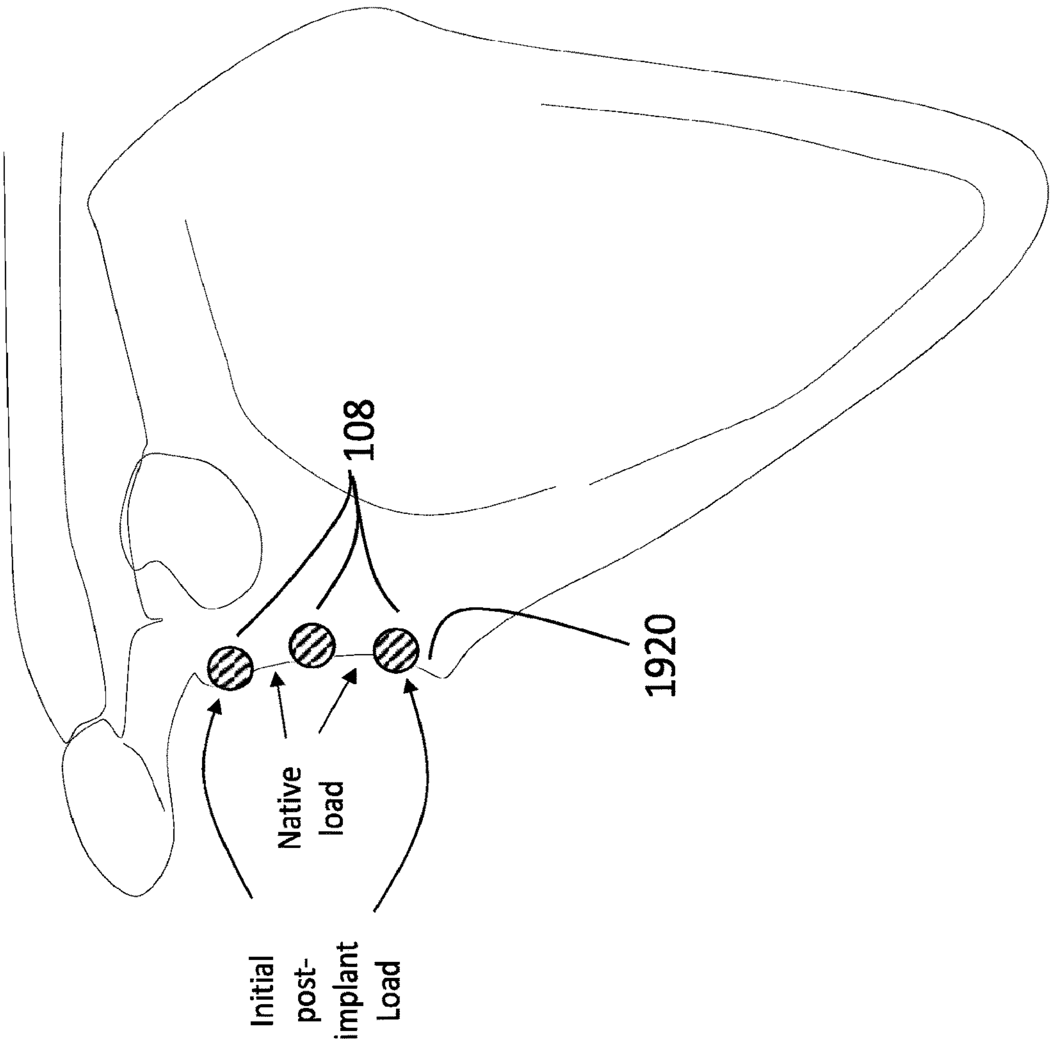
FIGS. 20A-20F show various non-limiting embodiments of configurations of implants that can be used in repairing damaged tissue in a ball and socket/convex-concave type joint.
Figure 20B:
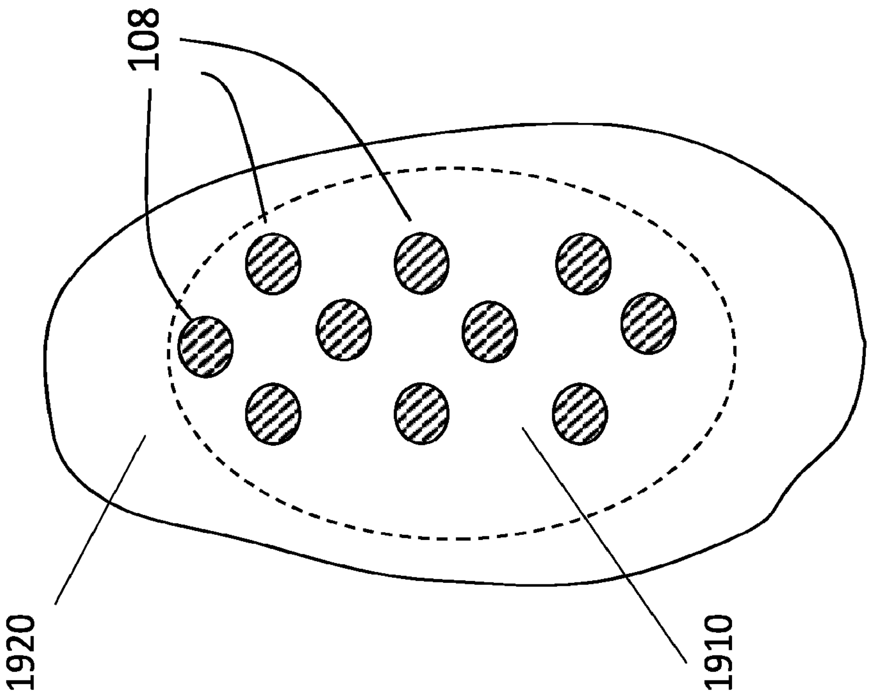

FIG. 20A shows an additional schematic of implants 108 positioned in an array, according to several embodiments disclosed herein. While this Figure schematically depicts the glenoid cavity 1920 and the humeral head 1910, it shall be appreciated that an array or mosaic of implants can be deployed in any type of joint space. FIG. 20A shows a side view of the glenoid cavity 1920 with the cortical bone region shown in crosshatch and a series of implants 108 placed along the concave glenoid surface. As depicted by the two arrows, native load from the humeral head but typically be positioned against the concave surface of the glenoid. Post-implantation, at least initially, the load from the humeral head is positioned against the plurality of implants. Needless to say, the load is not necessarily equally distributed across the implants, depending on where the humeral head 1910 is positioned within the glenoid cavity 1920, for example, based on movement of the arm. As mentioned above, this schematic figure does not depict the gap 122 that is formed around each implant 108 when it is initially positioned in place, though it shall be appreciated based on the disclosure herein, that the gap 122 is present and through the movement of the implant vis-a-vis the surrounding tissue, fibrous tissue, and then cartilage, is formed. FIG. 20B shows a schematic spacing view of an array of implants 108 positioned within the glenoid cavity. The humeral head 1910 is shown in phantom so as to not occlude the view of the implants 108. As noted above, the position of the implants 108 is driven largely by the location of the defect and thus need not be in any particular pattern or shape. However, when treating a large area, it may be desirable to position the implants 108 in a more defined pattern, for example in rows, in columns or in other geometric shapes or positions relative to the other implants positioned within the space.

Figure 20C:
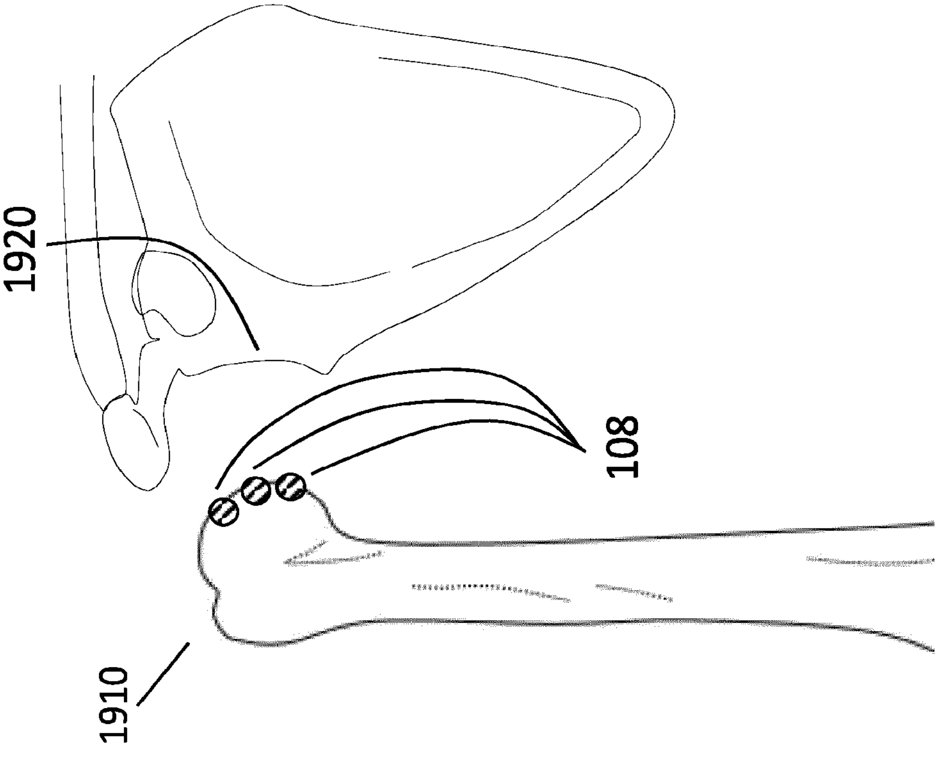
Figure 20D:
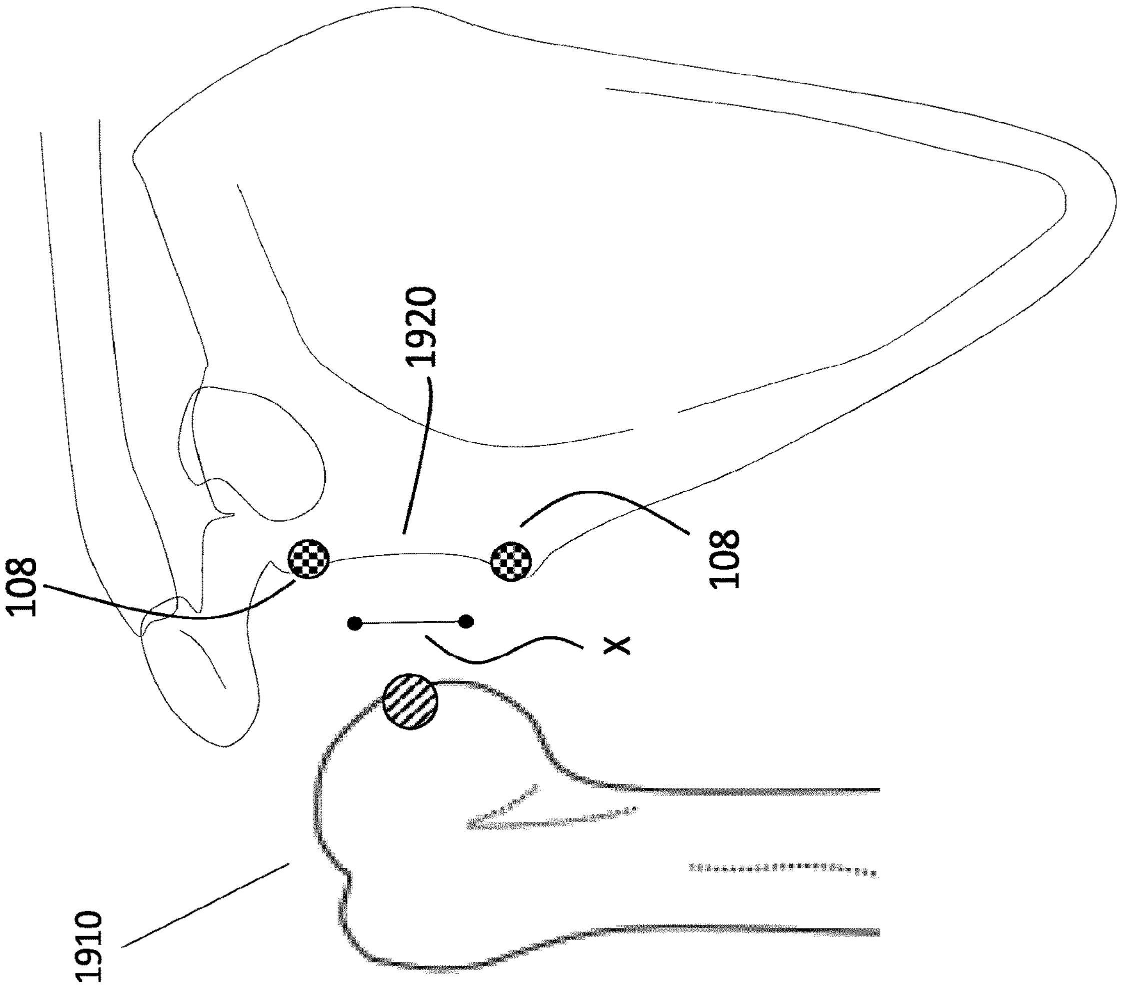
Figure 20E:
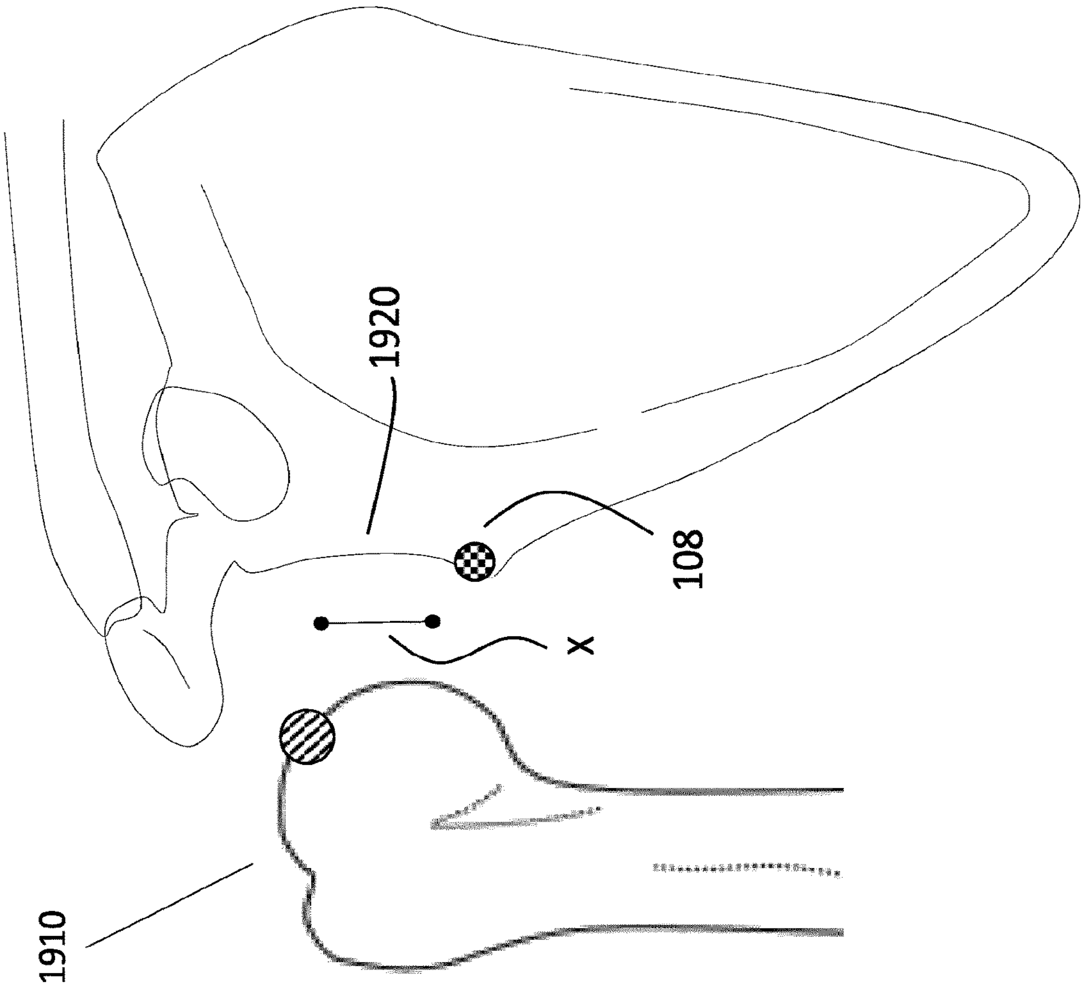
Figure 20F:
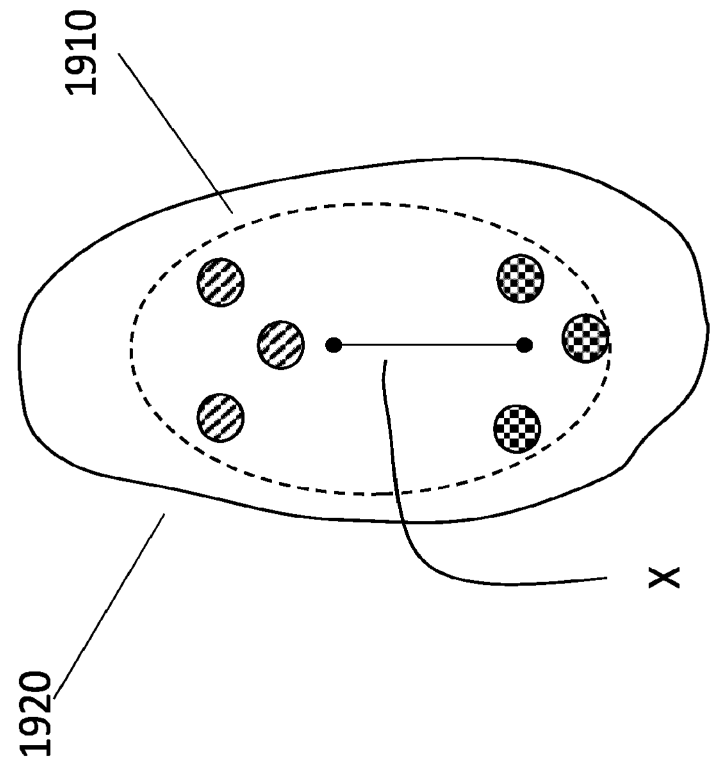

FIG. 20C depicts an additional embodiment in which an array of the implants 108 are positioned within the head of the humerus 1910, rather than within the glenoid cavity 1920, Turning now to FIG. 20D, this Figure schematically depicts an arrangement in which implants 108 are positioned both on the head of the humerus 1910 and within the glenoid cavity 1920. Depending on the embodiment, particularly based on the location of the defective regions of cartilage, it may be necessary to limit the range of motion X of the shoulder such that the implant positioned in the humerus does not come into contact with either of the implants positioned within the glenoid. While X is shown schematically as movement in the inferior-superior direction along the glenoid 1920, it shall be appreciated that implant 108 positioning should also take into account movement of the humeral head 1910 along the glenoid 1920 in other (non-illustrated) directions. FIG. 20E depicts another schematic of a similar situation where the single implant 108 is positioned on each of the head of the humerus 1910 and within the glenoid cavity 1920. Again, certain embodiments may require restriction of the range of motion X or repositioning of the implants to a single side of the joint to avoid the possibility of implant to implant contact during normal motion of the joint (including directions other than the inferior-superior motion depicted). FIG. 20F shows a facing view of the shoulder joint that depicts a similar embodiment in that the implants 108 are positioned on either side of the joint space, but done so in a manner that positioned the implants are further apart than the range of motion X of the humerus 1910 within the glenoid cavity 1920, thereby avoiding implant to implant contact during motion of the joint.

Figure 21A:
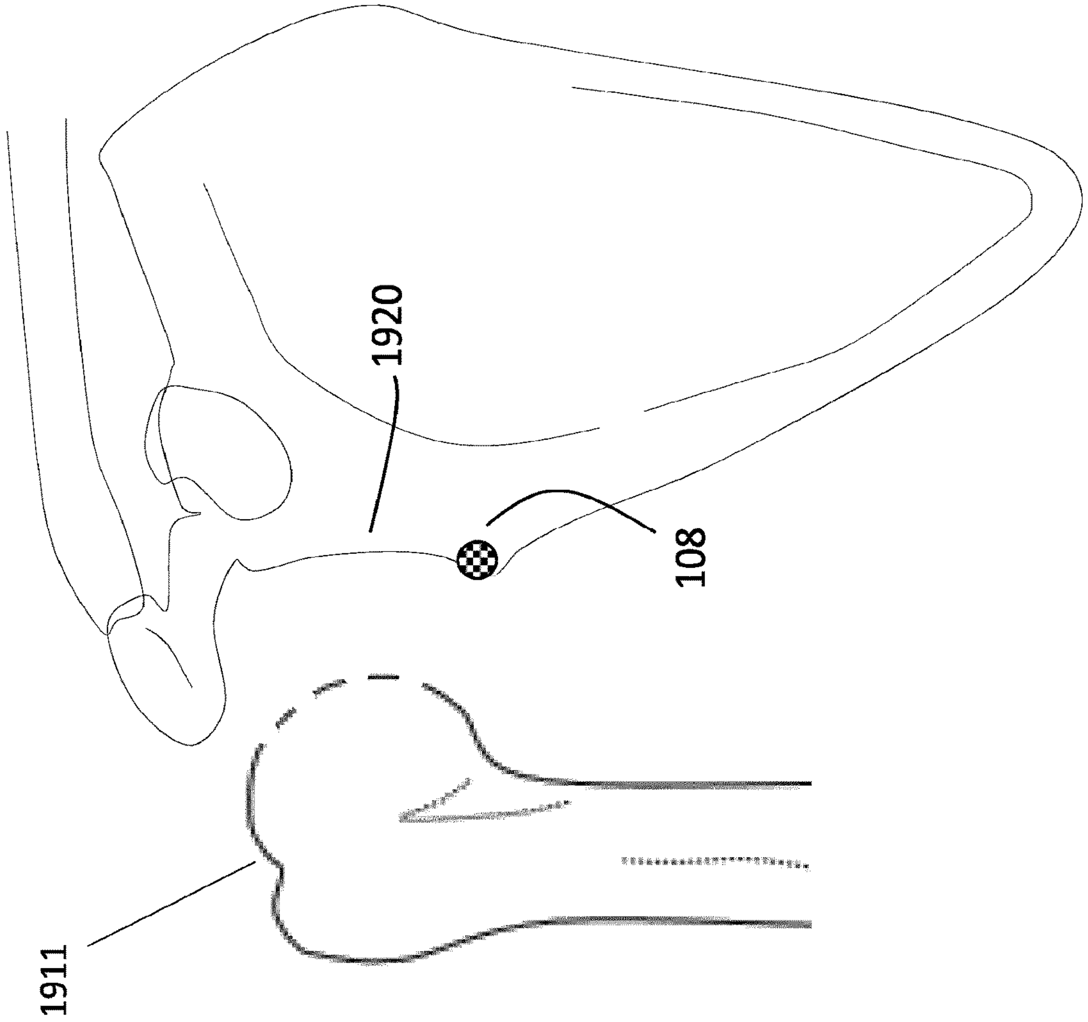
FIGS. 21A-21B depict additional non-limiting embodiments wherein an implant is positioned in one portion of a joint space, such as the glenoid cavity of the shoulder, and a replacement joint head is also used.
Figure 21B:
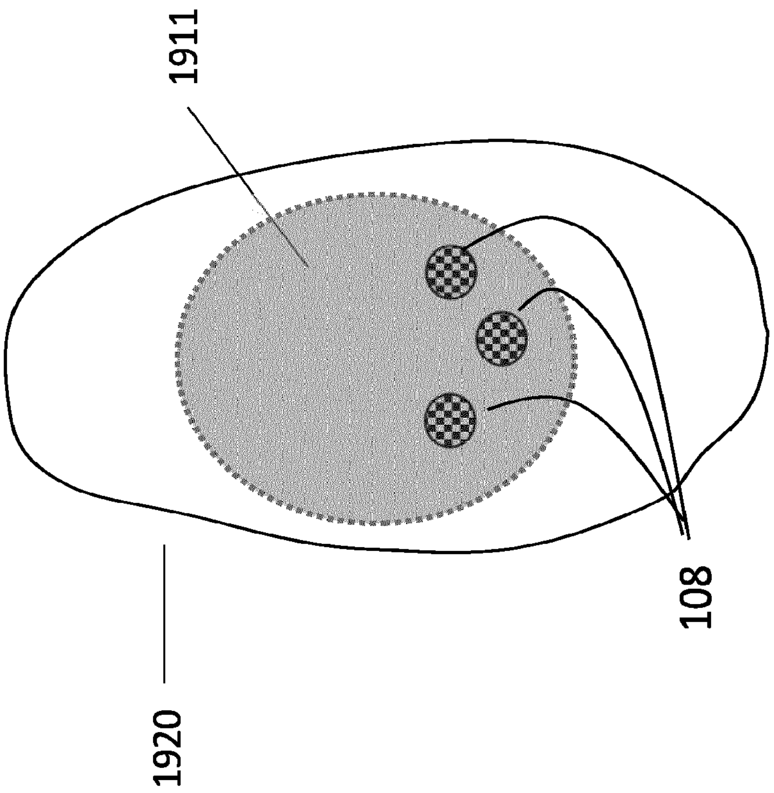

In the event that positioning of implants would likely cause implant to implant contact, or if an entire surface of a joint needed to be replaced due to severe damage, FIG. 21A-21B depict a non-limiting embodiments of an approach that could be used. Again, the interaction between the head of the humerus in the glenoid cavity is used by way of example only, and this approach could be used on any joint surface. FIG. 21A depicts an implant 108 positioned in the glenoid cavity 1920, per embodiments disclosed elsewhere herein. FIG. 21A also depicts a pyrocarbon humeral head 1911 (shown in dashed lines). Of note, in several embodiments, the use of a pyrocarbon humeral head 1911 (or other opposing joint surface) can facilitate cartilage formation on the opposing surface of the joint, in some embodiments working synergistically with the implant 108 on the opposing surface of the joint. Note that the pyrocarbon humeral head 1911 has a radius of curvature that is not the same as that of the glenoid cavity 1920 surface. However, in several embodiments, because an implant is positioned in the surface of the glenoid cavity 1920, the radius of the pyrocarbon humeral head 1911 can be closer to that of the natural humerus. In several embodiments, the radii differ enough to account for the step-up of the implant 108 positioned in the surface of the glenoid 1920 and to allow for smooth articulation of the joint. FIG. 21B depicts a facing view of an additional embodiment, wherein a plurality of implants 108 are positioned within the glenoid cavity surface 1920 (checkerboard) and thus are in between the glenoid cavity surface 1920 and the pyrocarbon humeral head 1911 (shown shaded).

While several embodiments disclosed herein related to implants 108 that are spherical, in some embodiments, an ellipsoid or more ovalized implant 108 can be used, as shown in FIG. 22A-22B. While these figures schematically depict the implant 108 positioned in a convex surface, it shall be appreciated that the characteristics disclosed herein are equally as applicable to an implant positioned within a concave surface. FIG. 22A depicts dimensions D1 and D2, which can vary depending on the embodiment and joint space in which repair is to be performed. While the dimensions may overlap, it shall also be that when D1=D2, a spherical implant as described above results. Depending on the embodiment, D1 can range from about 2 to about 3 mm, about 3 to about 4 mm, about 4 to about 5 mm, about 5 to about 6 mm, about 6 to about 7 mm, about 7 to about 8 mm, about 8 to about 9 mm, about 9 to about 10 mm, about 10 to about 11 mm, about 11 to about 12 mm, about 12 to about 13 mm, about 13 mm to about 14 mm, about 14 to about 15 mm and any diameter there between, including endpoints. Dimension D2 can vary as well, for example from about 2 to about 3 mm, about 3 to about 4 mm, about 4 to about 5 mm, about 5 to about 6 mm, about 6 to about 7 mm, about 7 to about 8 mm, about 8 to about 9 mm, about 9 to about 10 mm, about 10 to about 11 mm, about 11 to about 12 mm, about 12 to about 13 mm, about 13 mm to about 14 mm, about 14 to about 15 mm and any diameter there between, including endpoints. As pictured an ellipsoid implant may have a value of D1 that is at least about 10% more, about 20% more, about 30% more, about 40% more, about 50% more (or greater) as compared to the value of D2. In some embodiments, an ellipsoid implant may not allow for full 360 degree rotation (as is the case in some embodiments with a spherical implant). However, in several embodiments, the implant can still rotate in a plane approximately perpendicular to the articular surface (R1 of FIG. 22B). In other embodiments, the implant rotates in a plane approximately parallel to the articular surface (R2 of FIG. 22B). This rotational movement (even if only micro-movements) provides sufficient stimulation for deposition of fibrous tissue in the gap between the implant and recess generated to house the implant.

Figure 23A:
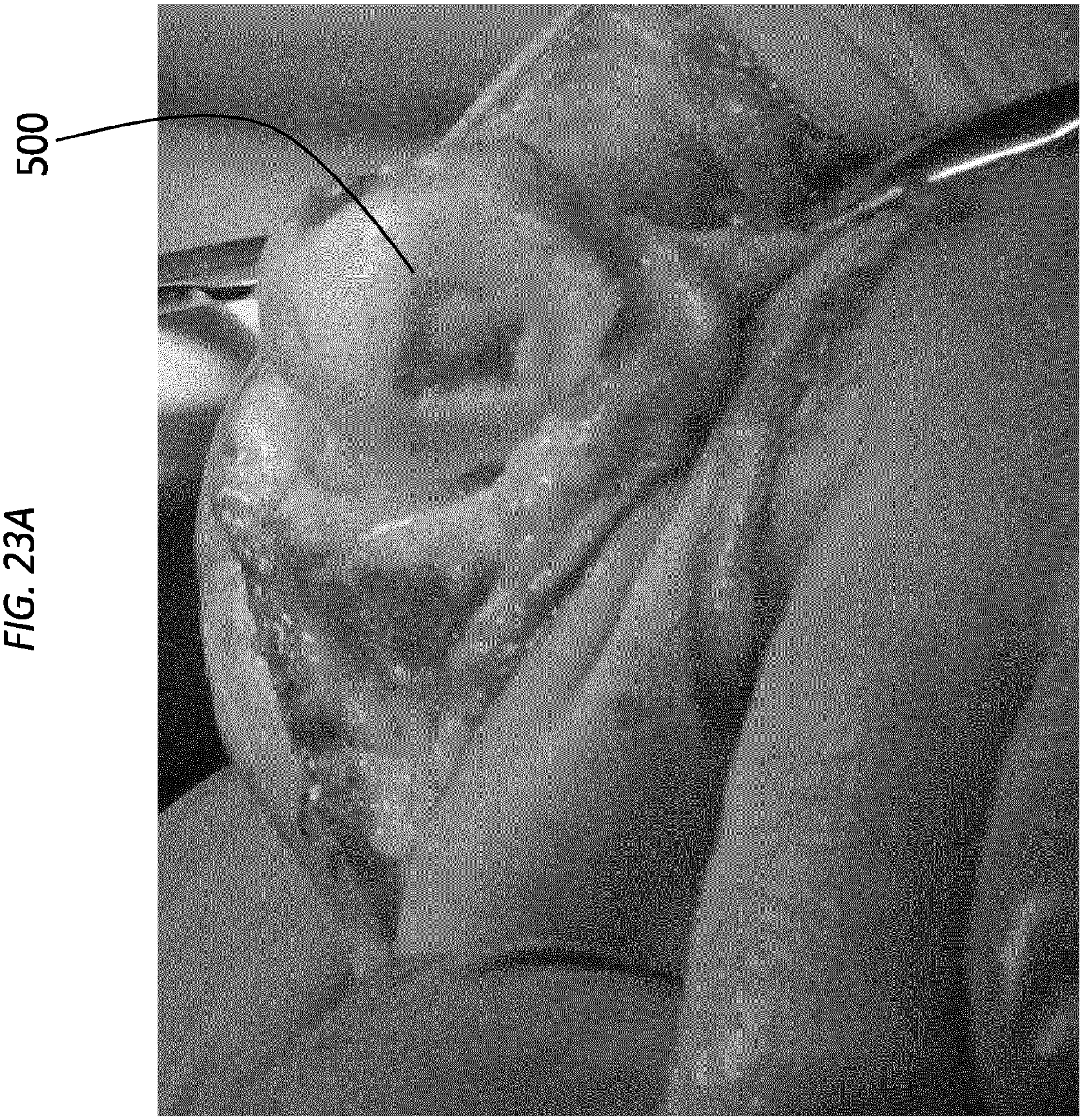
Figure 23B:

FIGS. 23A-23D relate to placement of an implant in the first MTP joint of a patient with damage to that joint. FIG. 23A shows the exposed articular surface of the joint with region of damage 500. FIG. 23B depicts the creation of an implant recess for receiving a spherical pyrocarbon implant. As discussed above, the recess has been created at the site of damage, such that the implant surface is substituted for the damaged region. The depth of the implant recess is drilled in proportion to the radius of curvature of the implant to be used. Given the size of the defect, in this example a sphere with a diameter of 8 mm was selected. Thus the recess accommodated the implant and allows for a “step-up” at the time of implantation, functioning to serve as a spacer from the opposing portion of the MTP joint. In several embodiments, the depth will allow the implant to pass through the cancellous bone and at least partially extend into the cortical bone.

FIG. 23C shows the implant 108 fully positioned within the recess created. Of note is the gap 122 that here can be seen as an annular void surrounding the implant. FIG. 23D shows an enlargement of the implant in position, with the annular gap identified by the dashed line and arrow. As discussed above, this gap is sized to allow for smooth articulation of the joint post-operatively (e.g., no "catching" of the joint) and facilitates the movement of the implant due to load on the joint and friction from the opposing joint surface, which thereby leads to deposition of fibrous tissue in the gap, with cartilage formation resulting subsequently.

Figure 23E:
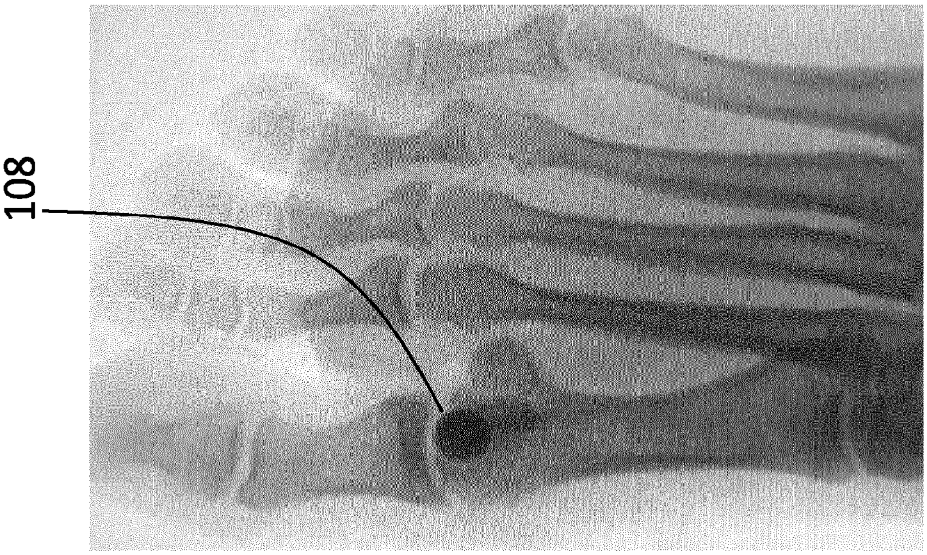

FIG. 23E shows an X-ray of the implant in position in the first MTP joint post-operatively. As shown, the implant need not be centered in the joint, but rather can be (depending on the embodiment) offset from a central plane and/or axis of a joint. As mentioned above, the location of the damage is a primary factor in determining the location of the implant (or implants).

By way of non-limiting example, the following disclosure relates to methods of implanting an implant, or implants, according to several embodiments disclosed herein. For example, in several embodiments, a method of regenerating cartilage is provided for herein, the method comprising, identifying a joint in a patient believed to have damaged or diseased cartilage, surgically accessing the joint space, identifying a region of cartilage in or around that joint space that comprises a region of damaged or diseased cartilage, creating a recess in the cartilage layer, wherein creating the recess involves removing at least a portion of the region of damage or diseased cartilage. The recess, in some embodiments, extends through the cartilage layer, into the cortical bone and optionally into the cancellous bone. Additionally, the recess is created with dimensions to accommodate an implant with a radius of curvature that is not equivalent to the radius of curvature in the portion of the joint in which the implant is to be positioned. In some embodiments, the implant is a spherical implant, while some embodiments utilize an ovalized implant. The implant is positioned in the formed recess, initially with at least a portion of the implant extending beyond the joint surface in order to serve as a spacer against the opposing portion of the joint space. As discussed herein, the implant is positioned in the recess with a gap (122 in the Figures) around the implant. After positioning, the opposing joint surfaces are re-oriented to their native position, with the implant having replaced the damaged or diseased region of cartilage. In some embodiments, a plurality of implants are positioned in the joint. Depending on the embodiment, the implants may be positioned on the same side of a given joint space, or on opposing sides of the joint space. In additional embodiments, the implant can optionally be positioned opposite the damaged region of cartilage. The surgical access to the joint space is subsequently closed. The joint space varies, depending on the embodiment, and can be an interphalangeal joint, a knee joint, an acetabulofemoral joint, a talocrural joint, a radiocarpal joint, an elbow joint, a metacarpophalangeal joint, or a metatarsophalangeal joint. In some embodiments, the implant or implants comprise a pyrocarbon implant, or optionally a pyrocarbon surface that faces the joint space. In several embodiments, the implant, surrounded by the gap, allows for two dimensional movement of the implant(s) wherein the two dimensional motion results in shear forces between the stimulating region of the implant and the healthy surrounding tissue. After a period of time, the shear forces between the implant and the healthy cartilage stimulate formation of fibrous tissue. Subsequently the formed fibrous tissue is transformed to articular cartilage.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention. The drawings are for the purpose of illustrating embodiments of the invention only, and not for the purpose of limiting it.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "implanting a cartilage-regenerating implant" include "instructing implantation of a cartilage regenerating implant." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers".

What is claimed is:

1. A method of stimulating regeneration of cartilage in an area of diseased cartilage in a layer of cartilage in a first bone of a joint, the method comprising:

forming a first recess in the first bone at the area of diseased cartilage, the area of diseased cartilage having a diameter, the first recess having a first depth configured to extend through the layer of cartilage and at least partially into a layer of underlying cortical bone, the first recess having a diameter greater than the diameter of the area of diseased cartilage; and positioning a first spherical implant within the first recess such that at least a portion of the first spherical implant extends out of the first recess to a height above the first bone that is less than a depth of the layer of cartilage, wherein the first spherical implant is rigid, wherein the first spherical implant is dimensioned to be smaller than the first recess so that the first spherical implant is capable of moving in two dimensions within the first recess resulting in shear forces between the first spherical implant and the cartilage and stimulates formation of fibrous tissue which subsequently transforms into cartilage, wherein the first spherical implant has the shape of a complete sphere.

2. The method of claim 1, wherein the first recess has a diameter configured to provide a discontinuity between a portion of healthy cartilage in the layer of cartilage and an outer surface of the first spherical implant when the first spherical implant is fully inserted into the first recess.

3. The method of claim 1, wherein the first recess comprises a square edge recess.

4. The method of claim 1, wherein the first spherical implant is dimensioned to rotate within the first recess about at least one axis.

5. The method of claim 1, wherein the first spherical implant is dimensioned to provide lateral movement on at least one axis within the first recess.

6. The method of claim 1, wherein a distance between the first spherical implant to an outer surface of the layer of cartilage is about 0.05 mm to about 5 mm.

7. The method of claim 1, wherein the first spherical implant is made of pyrocarbon.

8. The method of claim 1, comprising:

forming a second recess in the first bone of the joint at a second area of diseased cartilage, the second area of diseased cartilage having a second diameter, the second recess having a second depth configured to extend through the layer of cartilage and at least partially into the underlying layer of cortical bone, the second recess having a diameter greater than the diameter of the second area of diseased cartilage; and positioning a second spherical implant within the second recess, wherein the second spherical implant is dimensioned to be smaller than the second recess so that the second spherical implant is capable of moving in two dimensions within the second recess resulting in shear forces between the second spherical implant and the cartilage and stimulates formation of fibrous tissue which subsequently transforms into cartilage.

9. The method of claim 8, wherein the second recess has a diameter configured to provide a discontinuity between a second portion of healthy cartilage in the layer of cartilage and an outer surface of the second spherical implant when the second spherical implant is fully inserted into the second recess.

10. The method of claim 9, wherein the discontinuity comprises a step-up, and wherein the step-up has a height of about 0.05 mm to about 5 mm measured from the layer of cartilage.

11. The method of claim 9, wherein the discontinuity comprises a step-down, and wherein the step-down has a height of about 0.05 mm to about 5 mm measured from the layer of cartilage.

12. The method of claim 8, wherein the first recess comprises a square edge recess.

13. The method of claim 8, wherein the second recess comprises a square edge recess.

14. The method of claim 8, wherein the first recess comprises a spherical recess having an opening at a terminal end of the first bone, wherein a diameter of the opening is 50 to 75% of the diameter of the spherical recess.

15. The method of claim 8, wherein the second spherical implant is dimensioned to rotate within the second recess about at least one axis.

16. The method of claim 8, wherein the second spherical implant is dimensioned to provide lateral movement on at least one axis within the second recess.

17. The method of claim 8, wherein the second spherical implant is made of pyrocarbon.

18. The method of claim 1, wherein the first bone comprises a bone of an interphalangeal joint, a knee joint, an acetabulofemoral joint, a talocrural joint, a radiocarpal joint, an elbow joint, a metacarpophalangeal joint, or a metatarsophalangeal joint.

19. A method, comprising:

accessing a joint space located between a first bone and a second bone, the first bone having a layer of cartilage that includes an area of diseased cartilage;

forming a recess in the first bone at the area of the diseased cartilage such that a discontinuity is formed in the layer of cartilage;

inserting a rigid spherical implant into the recess formed in the first bone such that at least a portion of the rigid spherical implant extends above a surface of the first bone and engages an uninterrupted layer of cartilage disposed on the second bone, wherein the recess and the rigid spherical implant are relatively dimensioned such that, when the rigid spherical implant is disposed within the recess, the rigid spherical implant is capable of moving within the recess and generating shear forces that stimulate formation of fibrous tissue that subsequently transforms into cartilage on the first bone.

20. The method of claim 19, wherein a distance between a surface of the implant that is disposed above the surface of the first bone and a surface of the layer of the cartilage at a margin of the discontinuity is less than or equal to 5 mm.

* * * * *